(12) United States Patent
An et al.

(10) Patent No.: US 10,960,082 B2
(45) Date of Patent: Mar. 30, 2021

(54) TRIDENTATE CONNEXON AND USE THEREOF

(71) Applicant: NEWBIO THERAPEUTICS, INC., Shanghai (CN)

(72) Inventors: Deqiang An, Shanghai (CN); Nianhe Han, Shanghai (CN); Di Zeng, Shanghai (CN); Hang Yang, Shanghai (CN); Peng Zhu, Shanghai (CN); Mingzhen Li, Shanghai (CN); Li Jian, Shanghai (CN); Chun Yang, Shanghai (CN)

(73) Assignee: NEWBIO THERAPEUTICS, INC., Shanghai (CN)

( * ) Notice: Subject to any disclaimer, the term of this patent is extended or adjusted under 35 U.S.C. 154(b) by 54 days.

(21) Appl. No.: 14/807,234

(22) Filed: Jul. 23, 2015

(65) Prior Publication Data

US 2016/0015832 A1    Jan. 21, 2016

Related U.S. Application Data

(63) Continuation-in-part of application No. PCT/CN2014/070780, filed on Jan. 17, 2014.

(30) Foreign Application Priority Data

Jan. 23, 2013  (CN) .......................... 201310025021.4

(51) Int. Cl.
*A61K 47/48* (2006.01)
*A61K 47/68* (2017.01)
(Continued)

(52) U.S. Cl.
CPC ...... *A61K 47/6803* (2017.08); *A61K 47/6811* (2017.08); *A61K 47/6851* (2017.08);
(Continued)

(58) Field of Classification Search
None
See application file for complete search history.

(56) References Cited

U.S. PATENT DOCUMENTS 5,208,020 A    5/1993  Chari et al.
5,416,064 A    5/1995  Chari et al.
(Continued)

FOREIGN PATENT DOCUMENTS

EP    0 425 235 A2    5/1991
WO    2004/103272 A2   12/2004
(Continued)

OTHER PUBLICATIONS

Doronina et al. ("Doronina", Bioconjugate Chem, 2006, 17, 114-124).*

(Continued)

*Primary Examiner* — Karl J Puttlitz
(74) *Attorney, Agent, or Firm* — Ladas & Parry LLP

(57) ABSTRACT

Disclosed are a type of tridentate linkers and use thereof. The tridentate linkers can be used to prepare an antibody drug conjugates as represented by formula I, L-(T-A-D)$_n$    I wherein, L is an antibody, antibody fragment or protein; T is a tridentate linker part; A is a cleavable linker group or a noncleavable linker part; D is a drug part; n is an integer of 0-8. The structure of the tridentate linker part is as represented by formula II, (Continued)

1

2

3

4

5

6

7

8

9

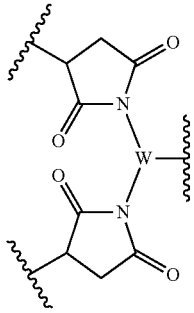

wherein, W is substituted aryl, heteroaryl, linear alkyl, cycloalkyl, heterocycloalkyl, or any combination thereof.

4 Claims, 13 Drawing Sheets

(51) Int. Cl.
 C07D 207/452 (2006.01)
 C07K 16/32 (2006.01)
(52) U.S. Cl.
 CPC ...... A61K 47/6855 (2017.08); A61K 47/6889 (2017.08); C07D 207/452 (2013.01); C07K 16/32 (2013.01); C07K 2317/92 (2013.01)

(56) References Cited

U.S. PATENT DOCUMENTS

| | | | |
|---|---|---|---|
| 5,606,040 A | 2/1997 | McGahren et al. | |
| 5,770,710 A | 6/1998 | McGahren et al. | |
| 6,884,869 B2 | 4/2005 | Senter et al. | |
| 7,129,261 B2 | 10/2006 | Ng et al. | |
| 7,276,497 B2 | 10/2007 | Chari et al. | |
| 7,473,796 B2 | 1/2009 | Chari et al. | |
| 7,498,298 B2 | 3/2009 | Doronina et al. | |
| 7,851,432 B2 | 12/2010 | Chari et al. | |
| 7,855,275 B2 | 12/2010 | Eigenbrot et al. | |
| 7,994,135 B2 * | 8/2011 | Doronina ............... | C07K 16/32 514/19.3 |
| 2007/0269447 A1 | 11/2007 | Chari et al. | |
| 2008/0096819 A1 | 4/2008 | Grabstein et al. | |
| 2010/0021543 A1 | 8/2010 | Rabuka et al. | |
| 2011/0158991 A1 | 6/2011 | Chari et al. | |
| 2011/0301334 A1 | 12/2011 | Bhakta et al. | |
| 2012/0121615 A1 | 5/2012 | Flygare et al. | |

FOREIGN PATENT DOCUMENTS

| | | |
|---|---|---|
| WO | 2005/040170 A2 | 5/2005 |
| WO | 2006/065533 A2 | 6/2006 |
| WO | 2006/069246 A2 | 6/2006 |
| WO | 2007/059312 A2 | 5/2007 |
| WO | 2007/130453 A2 | 11/2007 |
| WO | 2008/141044 A2 | 11/2008 |
| WO | 2009/026393 A2 | 2/2009 |
| WO | 2009/052249 A1 | 4/2009 |
| WO | 2010/081110 A1 | 7/2010 |
| WO | 2012/061590 A1 | 5/2012 |
| WO | 2012/074757 A1 | 6/2012 |

OTHER PUBLICATIONS

Caron et al. ("Caron" Org. Biomol. Chem. 2011, 9, 185-197).*
Girouard et al. ("Girouard", 2005, J. Am. Chem. Soc., 127, 559-566) (p. 29).*
Sun et al. ("Sun", Bioconjugate Chem., 2005, 16, 1282-1290) (Year: 2005).*
Creative Biolabs (https://www.creative-biolabs.com/adc/cysteine-based-conjugation.htm) (Year: 2017).*
Carter, P. J., et al., "Antibody-Drug Conjugates for Cancer Therapy", The Cancer Journal, vol. 14, No. 3, May/Jun. 2008, pp. 154-169.
Chari, R.V.J., "Targeted Cancer Therapy: Conferring Specificity to Cytotoxic Drugs", Accounts of Chemical Research, vol. 41, No. 1, Jan. 2008, pp. 98-107.
Senter, P.D., "Potent antibody drug conjugates for cancer therapy", Current Opinion in Chemical Biology, 2009, 13, pp. 235-244.
Teicher, B.A., "Antibody-Drug Conjugate Targets", Current Cancer Drug Targets, 2009, 9, pp. 982-1004.
Ducry, L., et al., "Antibody-Drug Conjugates: Linking Cytotoxic Payloads to Monoclonal Antibodies", Bioconjugate Chem. 2010, 21, pp. 5-13.
Lash, A., Making the Case for Antibody-Drug Conjugates, The Business & Medicine Report, Dec. 2010, pp. 32-38.
Casi, G., et al., "Antibody—drug conjugates: Basic concepts, examples and future perspectives", Journal of Controlled Release, 161, 2012, pp. 422-428.
Katz, J., et al., "Brentuximab Vedotin (SGN-35)", Clin Cancer Res, 17(20), Oct. 15, 2011, pp. 6428-6436.
Mathew, J., et al., "Trastuzumab emtansine in human epidermal growth factor receptor 2-positive breast cancer: a review", Current Opinion in Oncology, 2011, 23, pp. 594,600.
Dubowchik, G. M., et al., "Cathepsin B-Labile Dipeptide Linkers for Lysosomal Release of Doxorubicin from Internalizing Immunoconjugates: Model Studies of Enzymatic Drug Release and Antigen-Specific In Vitro Anticancer Activity", Bioconjugate Chem. 2002, 13, pp. 855-869.
Lazar, A. C., et al., "Analysis of the composition of immunoconjugates using size-exclusion chromatography coupled to mass spectrometry", Rapid Communications in Mass Spectrometry, 2005, 19, pp. 1806-1814.
Sun, M.M.C., et al., "Reduction-Alkylation Strategies for the Modification of Specific Monoclonal Antibody Disulfides", Bioconjugate Chem. 2005, 16, pp. 1282-1290.
Boswell, C. A., et al., "Impact of Drug Conjugation on Pharmacokinetics and Tissue Distribution of Anti-STEAP1 Antibody-Drug Conjugates in Rats", Bioconjugate Chemistry, 2011, 22, pp. 1994-2004.
McDonagh, C.F., et al., "Engineered antibody—drug conjugates with defined sites and stoichiometries of drug attachment", Protein Engineering Design & Selection, vol. 19, No. 7, 2006, pp. 299-307.
Junutula, J.R., et al., "Site-specific conjugation of a cytotoxic drug to an antibody improves the therapeutic index", Nature Biotechnology, vol. 26, No. 8, Aug. 2008, pp. 925-932.
Junutula, J.R., et al., "Engineered Thio-Trastuzumab-DM1 Conjugate with an Improved Therapeutic Index to Target Human Epidermal Growth Factor Receptor 2—Positive Breast Cancer", Clin Cancer Res, 16(19), Oct. 1, 2010, pp. 4769-4778.
Liberatore, F. A., et al., "Site-Directed Chemical Modification and Cross-Linking of a Monoclonal Antibody Using Equilibrium Transfer Alkylating Cross-Link Reagents", Bioconjugate Chem. vol. 1, No. 1, 1990, pp. 36-50.
del Rosario, R. B., et al., "Sulfhydryl Site-Specific Cross-Linking and Labeling of Monoclonal Antibodies by a Fluorescent Equilibrium Transfer Alkylation Cross-Link Reagent", Bioconjugate Chem., 1990, 1, pp. 51-59.
BioSpectrum, 39, Mar. 14, 2012, 2 pages.
Antonow, D., et al., "Solution Structure of a 2:1 C2-(2-Naphthyl) Pyrrolo[2,1-c][1,4]benzodiazepine DNA Adduct: Molecular Basis for Unexpectedly High DNA Helix Stabilization", Biochemistry 2008, 47, 00. 11818-11829.
First Office Action in respect of counterpart Application No. EP 2949343 dated Oct. 27, 2015.
Second Office Action in respect of counterpart Application No. EP 2949343 dated Jul. 5, 2016.
Third Office Action in respect of counterpart Application No. EP 2949343 dated Jan. 23, 2017.

(56) References Cited

OTHER PUBLICATIONS

Karine Caron, et al.: Dramatic increase of quench efficiency in "spacerless" dimaleimide fluorogens: The Royal Society of Chemistry: Organic & Biomoleetilar Chemistry: 2011:9: pp. 185-097.

* cited by examiner

1

2

3

4

5

6

7

8

9

US 10,960,082 B2

TRIDENTATE CONNEXON AND USE THEREOF

CROSS-REFERENCE APPLICATIONS

This application is a continuation-in-part of International Application No. PCT/CN2014/070780 filed Jan. 17, 2014, which was published on 31 Jul. 2014, with International Publication Number WO 2014/114207 A1, and which claims priority from Chinese Application No. 201310025021.4 filed Jan. 23, 2013, the content of which is incorporated herewith by reference.

FIELD OF THE INVENTION

The invention relates to pharmaceutical treatment of tumors or other diseases via antibody drug conjugates (ADCs). The invention further relates to preparation of ADCs utilizing a specific tridentate linker to control the drug/antibody ratio (DAR).

BACKGROUND ARTS

As novel targeted therapeutic agents, antibody drug conjugates (ADCs) open a new era for the treatment of tumors of different kinds (Carter, et al. 2008, Cancer J. 14: 154-169; Chari, et al. 2008, Acc. Chem. Res. 41: 98-107; Senter, et al. 2009, Curr. Opin. Chem. Biol. 13: 235-244; Teicher, et al. 2009, Curr. Cancer Drug Targets, 9: 982-1004; Ducry, et al. 2010, Bioconjugate Chem. 21: 5-13; Lash, et al. 2010, In vivo: The Business & Medicine Report 32-38; Casi, et al. 2012, J. Control. Rel. 161: 422-428). Pioneered by Seattle Genetics, Inc. and ImmunoGen Inc., many multi-national and start-up pharmaceutical companies are involved in ADC programs. As disclosed by wall-street reports in May 2011, a total of 36 ADC programs were in either preclinical or clinical trials. In August 2011, Adcetris™, developed by Seattle Genetics, Inc., was approved by FDA for treatment of Hodgkin lymphoma (HL) and relapsed systemic anaplastic large cell lymphoma (sALCL) (Katz, et al. 2011, Clin. Cancer Res. 17: 6428-6436). Another ADC drug from Genentech for treatment of breast cancer, T-DM1, obtained good results in phase 3 clinical trials, and hopefully will be approved by FDA in early 2013 (Mathew et al. 2011, Curr. Opin. Oncol. 23: 594-600).

An ADC drug is composed of three independent parts: an antibody or antibody-like ligand, small molecular drugs, and linkers that conjugate the drugs to the ligand. The mechanism of action (MOA) of an antibody drug conjugate is described as follows. An antibody or antibody-like ligand targets specific cell surface protein receptors (antigens). Once binding to the antigens, the binding complex will internalize and thus deliver the linked drugs into the cell. The antibody or antibody-like ligand will be digested by enzymes, or the linkers will be cleaved, via either way the small cytotoxic drugs could be released in an active form and kill the cells. Small cytotoxic drugs used in ADCs are required to be highly potent, normally 10-1000 folds higher than those first-line chemotherapy drugs in use. Currently used cytotoxic drugs for ADCs mainly include maytansinoids (EP 0425235; U.S. Pat. Nos. 5,208,020, 5,416,064; 7,276,497, 7,473,796, 7,851,432; US 2007/0269447, 2011/0158991; WO 2004/103272, 2012/061590), auristatins (U.S. Pat. Nos. 6,884,869, 7,498,298), calicheamicins (U.S. Pat. Nos. 5,606,040, 5,770,710), doxorubicins (Dubowchik, et. al. 2002, Bioconjugate Chem. 13: 855-869), duocarmycins and CC-1065 (U.S. Pat. No. 7,129,261), and pyrrolo[2,1-c][1,4]benzodiazepine (PBD) dimers (WO 2005/040170), etc. Linkers used in ADCs need to meet several prerequisites: the linkers need to be stable when circulating in human plasma to prevent early release of cytotoxic drugs; upon internalized into the tumor cell, the cleavable linkers could be cleaved under certain condition to release the cytotoxic drugs, while for non-cleavable linkers, the drug moieties are released in an active form that contains cytotoxic drug, linker and amino acid residue derived from the protease-degraded ligand.

In most clinical ADC structures, highly-potent cytotoxic drugs are normally linked, via different linkers, to the ε-amino group of lysine residues or hinge-region cysteine residues (after full/partial reduction of interchain disulfide bonds). The optimized DARs are preferred to be 2~4. The large number of ε-amino groups of lysine residues (~80/mAb) on the surface of antibodies and the non-selective conjugation mode lead to the uncertainty of conjugation sites and conjugated drug numbers, and thus afford ADC product with high heterogeneity. For example, T-DM1 (average DAR ~3.5) has a DAR value distribution of 0-8 (Lazar, et al. 2005, Rapid Commun. Mass Spectrom. 19: 1806-1814). Similarly, although an antibody contains only four reducible inter-chain disulfide bonds in the hinge area, it must be partially reduced and conjugated to give ADCs with optimal average DAR 2~4 (Sun, et al. 2005, Bioconjugate Chem. 16: 1282-1290). As generally used reducing agents (DTT, TCEP, etc) couldn't selectively reduce the hinge-region disulfide bonds, the conjugation products thus obtained are not homogeneous either, containing conjugates with DAR of 0, 2, 4, 6 and 8. Even for a fraction with specific DAR value, it is a mixture that contains conjugates with drugs coupled at different conjugation sites. The heterogeneity of ADC products may ultimately lead to different PK, efficacy, and toxicity properties for different fractions. For example, fractions with higher DAR have, in some cases, been reported to clear more rapidly and contribute to more severe toxicity (Boswell, et. al. 2011, Bioconjugate Chem. 22: 1994-2004).

To overcome the issue of high heterogeneity of ADC products, site-specific conjugation technologies have been the hot spots recently, which control both conjugation sites and stoichiometrics of drug loading. Seattle Genetics Inc. reported partial replacement of cysteines that form the interchain disulfide bonds in cAC10 with serine, to reduce the eight potential conjugation sites down to 4 or 2 (WO 2006/065533; Mcdonagh, et al. 2006, Protein Eng. Des. Sel. 19: 299-307). The ADCs with defined sites and stoichiometrics of the drug loading show similar in vitro and in vivo properties to that of the corresponding purified ADC fraction from parental heterogeneous ADCs, including antitumor activity, pharmacokinetics and maximum tolerated dose. Using leads phage display-based method to predict suitable conjugation sites, Genentech engineered cysteine substitutions at positions on light and heavy chains that provide reactive thiol groups and do not perturb immunoglobulin folding and assembly, or alter antigen binding (U.S. Pat. No. 7,855,275; US 2011/0301334; WO 2008/141044, 2009/052249; Junutula, et al. 2008, Nat. Biotechnol. 26: 925-933; Junutula, et al. 2010, Clin. Cancer Res. 16: 4769-4778). ADCs produced based on this technology showed favorable in vivo properties of the near-homogenous composition. Different from the above-mentioned technologies, Ambrx (WO 2006/069246, 2007/059312), Allozyne (US 2008/0096819; WO 2007/130453, 2009/026393), Sutro (WO 2010/081110) and Redwood (US 2010/0210543) all developed recombinant antibody/protein technologies, which incorporate unnatural amino acids at certain sites of antibodies or proteins, and thus allow site-specific modification including pegylation, glycosylation or antibody drug conjugation. Despite the advantages of controllable conjugation sites and stoichiometrics of the drug loading, the antibodies or proteins in these technologies are all genetically engineered. Such mutagenesis may be time consuming and not cost effective, as substantial work and special care need to be taken to screen the antibodies with favorable mutation sites for further drug conjugation or pegylation.

Considering these problems, site-specific conjugation via simple chemistry methods may be more cost effective and thus more attractive. A class of equilibrium transfer alkylating cross-link (ETAC) reagents were reported that reacted with reduced/partially reduced antibody to give cross-linked structures (Liberatore, et al. 1990, Bioconjugate Chem. 1: 36-50; del Rosario, et al. 1990, Bioconjugate Chem. 1: 51-59). The interchain cross-linking products had modest yields (~30%) and low homogeneity, containing mixtures of 0 to 4 cross-linking components. Korea-based LegoChem Biosciences (LCB) is working on a technology that consists of site-specific functionalization and orthogonal drug conjugation step, but no detail information are disclosed (BioSpectrum, 2012, 39).

Based on above issues, highly efficient, simple, and practical chemical coupling methods for ADC production are greatly needed in this field.

SUMMARY OF THE INVENTION

This object of the invention is to provide an innovative tridentate linkers that could be used to produce ADCs via chemical coupling methods.

In the first aspect, this invention disclosed antibody drug conjugates of formula I:

L-(T-A-D)$_n$    I

Wherein: L is antibody, antibody fragment, or protein; T is tridentate linker; A is other linker part, D is cytotoxic drug, n is an integer of 0-8.

The structure of tridentate linker is as represented by formula II:

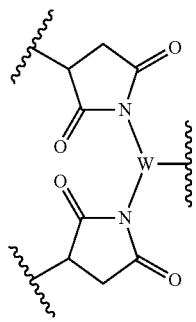

II wherein: W is substituted aryl, heteroaryl, alkyl, cycloalkyl, heterocycloalkyl, or any combination thereof.

In a preferred embodiment, A is cleavable linker combination or a noncleavable linker; A is better as represented by formula III or IV:

C-E$_e$-F$_f$    III

G$_g$    IV wherein: C is a cleavable linker; E is a self-immolative linker, F is an optional self-immolative linker; e or f is an integer of 0-5; G is a noncleavable linker; g is an integer of 0-5.

In a preferred embodiment, the antibody drug conjugates is as represented by formula V, VI, VII or VIII:

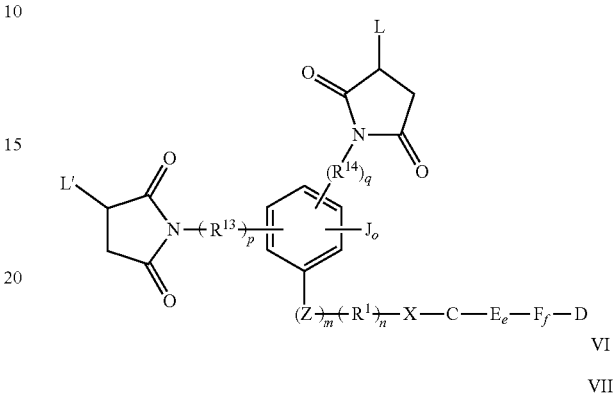

V

VI

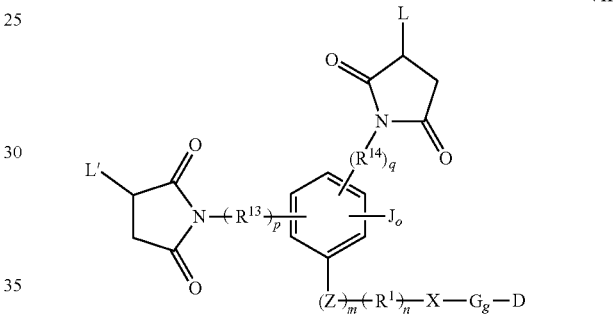

VII

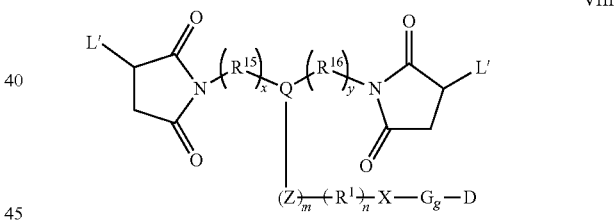

VIII wherein: L is an antibody, antibody fragment, or protein; L' is an antibody, antibody fragment, protein or other group (thio-containing group like cysteine); when L' is an antibody or antibody fragment, L'=L; Z is O, S, NR$^2$, C(=O)O, C(=O)NR$^3$, C(=S)O, C(=S)NR$^4$, C(=S)S, NR$^5$C(=O)NR$^6$, NR$^7$C(=S)NR$^8$, OC(=O)NR$^9$; m is 0 or 1; R$^2$, R$^3$, R$^4$, R$^5$, R$^6$, R$^7$, R$^8$, and R$^9$ is independently selected from H, linear alkyl, cycloalkyl, heterocycloalkyl, alkenyl, alkynyl, aryl, heteroaryl; R$^1$ is linear alkyl, cycloalkyl, heterocyclyalkyl, alkenyl, alkynyl, aryl, heteroaryl, polyethylene glycol) chain, or any combination thereof; n is an integer of 0-8; X is —NR$^{10}$—, —O—, —S—, —C(=O)—, —C(=S)—, —NR$^{11}$C(=O)—, —NR$^{12}$C(=S)—, —OC(=O)—, —OC(=S)—; R$^{10}$, R$^{11}$, and R$^{12}$ is independently selected from H, linear alkyl, cycloalkyl, heterocycloalkyl, alkenyl, alkynyl, aryl, heteroaryl; J is substitution group, including, but not limited to H, halogen, nitro, cyano, hydroxyl, alkoxy, amino, amide, ester, sulfamide, urea, linear alkyl, cycloalkyl, heterocycloalkyl, alkenyl, alkynyl, aryl, heteroaryl; o is 0, 1, 2 or 3; R$^{13}$, R$^{14}$, R$^{15}$ and R$^{16}$ is independently selected from linear alkyl, cycloalkyl, heterocycloalkyl, alkenyl, alkynyl, aryl, heteroaryl, or any combination thereof; Q is N or $CR^{17}$; $R^{17}$ is independently selected from H, linear alkyl, cycloalkyl, heterocycloalkyl, alkenyl, alkynyl, aryl, and heteroaryl; p, q is an integer of 0-8; x, y is an integer of 0-8, and $x+y \geq 1$.

In a preferred embodiment, the antibody is referred to an antibody that targets a receptor or tumor-related antigen on cell surface.

In a preferred embodiment, the drug is referred to cytotoxic, anti-autoimmune or anti-inflammation drug.

In the second aspect, the invention provides a tridentate linker of formula 1:

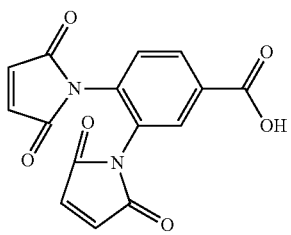

1

In the third aspect, the invention provides a tridentate linker of formula 3:

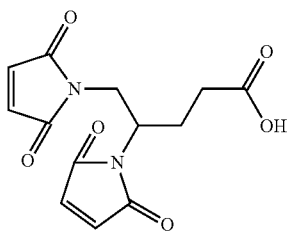

3

In the fourth aspect, the invention provides a tridentate linker of formula 4:

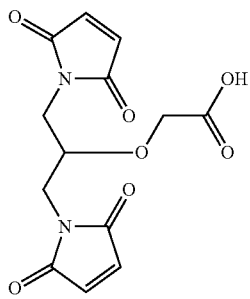

4

In the fifth aspect, the invention provides a tridentate linker of formula 5:

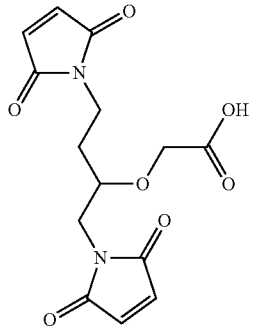

5

In the sixth aspect, the invention provides a tridentate linker of formula 6:

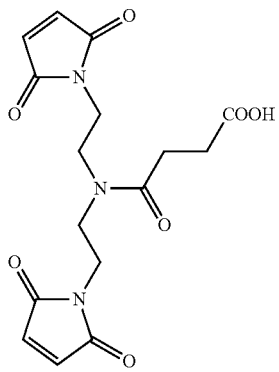

6

In the seventh aspect, the invention provides a use of a tridentate linker of formula IX in preparing antibody drug conjugates:

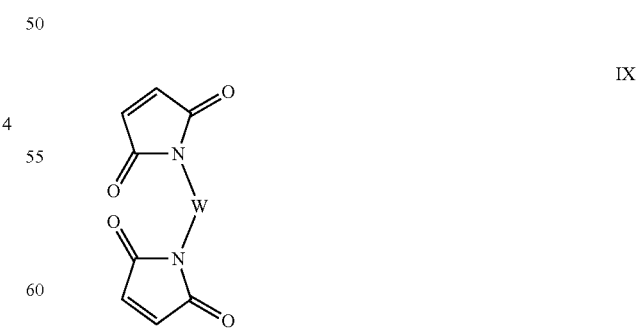

IX wherein: W is substituted aryl, heteroaryl, linear alkyl, cycloalkyl, heterocycloalkyl, or any combination thereof.

In a preferred embodiment, the tridentate linkers is as represented by formula 1, 2, 3, 4, 5, or 6:

1

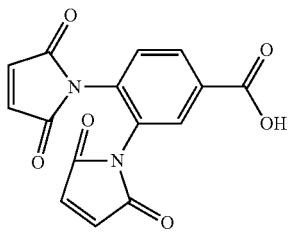

2

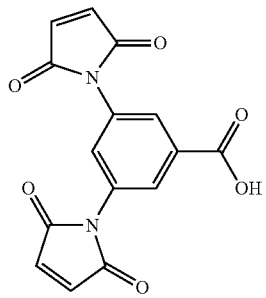

3

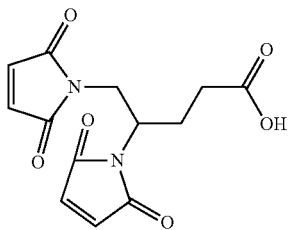

4

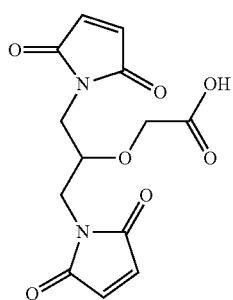

5

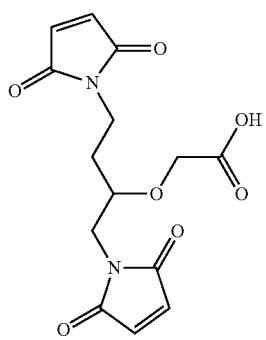

-continued

6

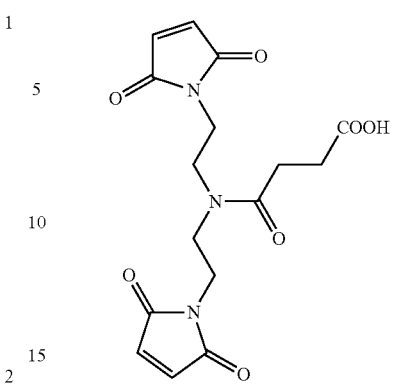

In summary, the invention provides a highly efficient, simple, and practical chemical coupling method.

DETAILED DESCRIPTION OF THE INVENTION

Figure 1:
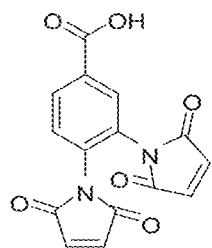
FIG. 1 shows the structures of the six specific tridentate linkers and three simplified bidentate linkers referred by the invention.
Figure 1:
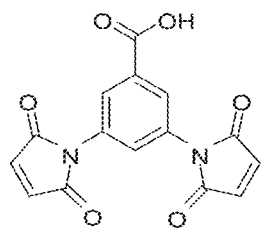
Figure 1:
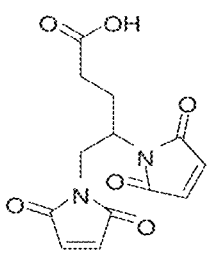
Figure 1:
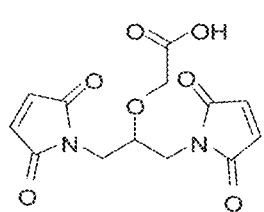
Figure 1:
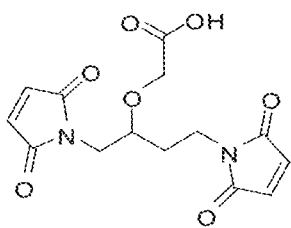
Figure 1:
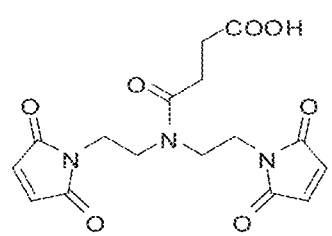
Figure 1:
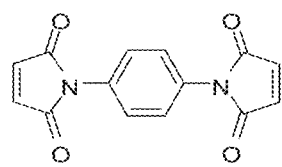
Figure 1:
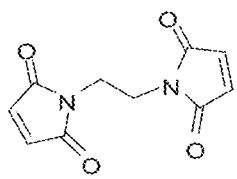
Figure 1:
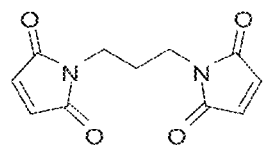

Through extensive study, the inventor surprisingly found that tridentate linker could completely/partially crosslink the antibody heavy-heavy and heavy-light chains. Furthermore, the inventor found that the ADCs obtained via above coupling method have narrower DAR distributions, compared to those of traditional antibody drug conjugates.

Specifically, the present invention provides tri dentate linkers, which include two maleimide groups and a third coupling group. The two maleimide groups are used to crosslink the interchain thiol groups (after reduction of interchain disulfide bond), while the third group is used to coupling with small molecule drug or drug-linker unit.

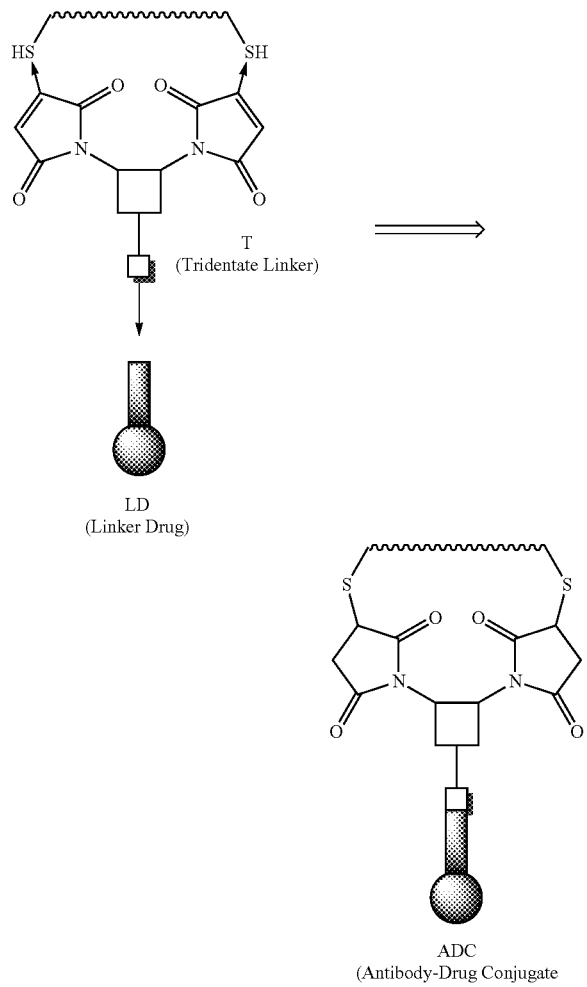

The ADCs thus made can be used to selectively deliver drugs to target cell groups, for example, tumor cells. The antibody drug conjugates will bind specifically to the cell surface proteins, and the binding complex will be internalized rapidly by the cells. Once internalized, the cytotoxic drug will be released in certain active form and take effects. The antibody includes chimeric, humanized, or human antibody; antibody fragment that can bind to antigen; or Fc fused protein; or protein. The drug is highly potent cytotoxic drug, including, but not limited to, maytansinoids, auristatins, calicheamicins, doxorubicins, CC-1065 and duocarmycins derivatives, and PBD dimers, etc. Under certain conditions, the drug could be poly(ethylene glycol). The drug itself, or drug-linker units, could be coupled to antibody via tridentate linkers, producing partially inter-chain crosslinked conjugates. Compared to traditional ones, the antibody drug conjugates based on this invention has much narrower DAR distribution, and thus greatly improve both structurally and pharmacologically homogeneities.

Definition

As used herein, the terms "antibody" or "antibody unit" includes any unit of an antibody that binds or reactively associates or complexes with a receptor, antigen or other receptive moiety associated with a given target-cell population within its scope. An antibody can be any protein or protein-like molecule that binds to, complexes with, or reacts with a moiety of a cell population sought to be therapeutically or otherwise biologically modified.

Antibody comprising the ADCs of the invention preferably retains the antigen binding capability of their native, wild type counterparts. Thus, antibodies of the invention are capable of binding, preferably specifically, to antigens. Such antigens include, for example, tumor-associated antigens (TAA), cell surface receptor proteins and other cell surface molecules, cell survival regulatory factors, cell proliferation regulatory factors, molecules associated with (for e.g., known or suspected to contribute functionally to) tissue development or differentiation, lymphokines, cytokines, molecules involved in cell cycle regulation, molecules involved in vasculogenesis and molecules associated with (for e.g., known or suspected to contribute functionally to) angiogenesis. The tumor-associated antigen may be a cluster differentiation factor (i.e., a CD protein). An antigen to which an antibody of the invention is capable of binding may be one or a subset of the above-mentioned categories, wherein the other subset(s) of said category comprise other molecules/antigens that have a distinct characteristic (with respect to the antigen of interest).

Antibodies used in ADCs include, but not limited to, antibodies against cell surface receptors and tumor-associated antigens (TAA). Such tumor-associated antigens are known in the art, and can be prepared for use in generating antibodies using methods and information which are well known in the art. In attempts to discover effective cellular targets for cancer diagnosis and therapy, researchers have sought to identify transmembrane or otherwise tumor-associated polypeptides that are specifically expressed on the surface of one or more particular type(s) of cancer cell as compared to on one or more normal non-cancerous cell(s). Often, such tumor-associated polypeptides are more abundantly expressed on the surface of the cancer cells as compared to on the surface of the non-cancerous cells. The identification of such tumor-associated cell surface antigen polypeptides has given rise to the ability to specifically target cancer cells for destruction via antibody-based therapies.

Examples of TAA include, but are not limited to, Tumor-Associated Antigens (1)-(36) listed below. For convenience, information relating to these antigens, all of which are known in the art, is listed below and includes names, alternative names, Genbank accession numbers. Nucleic acid and protein sequences corresponding to TAA (1)-(36) are available in public databases such as GenBank. Tumor-associated antigens targeted by antibodies include all amino acid sequence variants and isoforms possessing at least about 70%, 80%, 85%, 90%, or 95% sequence identity relative to the sequences identified in the cited references, or which exhibit substantially the same biological properties or characteristics as a TAA having a sequence found in the cited references.

Tumor-Associated Antigens (1)-(36):
(1) BMPR1B (bone morephogenetic protein receptor-type IB, Genbank accession no. NM_001203);
(2) E16 (LAT1, SLC7A5, Genbank accession no. NM_003486);
(3) STEAP1 (six transmembrane epithelial antigen of prostate, Genbank accession no. NM_012449);
(4) 0772P (CA125, MUC16. Genbank accession no. AF361486);
(5) MPF (MPF, MSLN, SMR, megakaryocyte potentiating factor, mesothelin, Genbank accession no. NM_005823):
(6) Napi3b (NAPI-3B, NPTIIb, SLC34A2, solute carrier family 34 (sodium phosphate) member 2, type II sodium-dependent phosphate transporter 3b, Genbank accession no. NM_006424);
(7) Sema 5b (FLJ10372, KIAA1445, Mm.42015, SEMA5B, SEMAG, Semaphorin 5b Hlog, sema domain, seven thrombospondin repeats (type 1 and type 1-like), transmembrane domain (TM) and short cytoplasmic domain, (semapborin) 5B, Genbank accession no. AB040878);
(8) PSCA hlg (2700050C12Rik, C530008016Rik, RIKEN cDNA 2700050C12, RIKEN CDNA2700050C12 gene, Genbank accession no. AY358628);
(9) ETBR (Endothelin type B receptor, Genbank accession no. AY275463);
(10) MSG783 (RNF124, hypothetical protein FLJ20315, Genbank accession no. NM_017763);
(11) STEAP2 (HGNC_8639, IPCA-1, PCANAP1, STAMP1, STEAP2, STMP, prostate cancer associated gene 1, prostate cancer associated protein 1, six transmembrane epithelial antigen of prostate 2, six transmembrane prostate protein, Genbank accession no. AF455138);
(12) TrpM4 (BR22450, FLJ20041, TRPM4, TRPM4B, transient receptor potential cation channel, subfamily M, member 4, Genbank accession no. NM_017636);
(13) CRIPTO (CR, CR1, CRGF, CRIPTO, TDGF1, teratocarcinoma-derived growth factor, Genbank accession no. NP_003203 or NM_003212;
(14) CD21 (CR2 (Complement receptor 2) or C3DR (C3d/ Epstein Barr virus receptor) or Hs. 73792, Genbank accession no. M26004);
(15) CD79b (CD79B, CD79β, IGb (immunoglobulin associated beta), B29, Genbank accession no. NM_000626);
(16) FcRH2 (IFGP4, IRTA4, SPAP1A (SH2 domain containing phosphatase anchor protein 1a), SPAP1B, SPAP1C, Genbank accession no. NM_030764);
(17) HER2 (ErbB2, Genbank accession no. M11730);
(18) NCA (CEACAM6, Genbank accession no. M18728);
(19) MDP (DPEP1, Genbank accession no. BC017023);
(20) IL20Rα (IL20Ra, ZCYTOR7, Genbank accession no. AF184971);
(21) Breviean (BCAN, BEHAB, Genbank accession no. AF229053);
(22) EphB2R (DRT, ERK, Hek5, EPHT3, Tyro5, Genbank accession no. NM_004442);
(23) ASLG659 (B7h, Genbank accession no. AX092328);
(24) PSCA (Prostate stem cell antigen precursor, Genbank accession no. AJ297436);
(25) GEDA (Genbank accession no. AY260763);
(26) BAFF-R (B-cell activating factor receptor, BLys receptor 3, BR3, Genbank accession no. AF116456);
(27) CD22 (B-cell receptor CD22-β form, Genbank accession no. AK026467);
(28) CD79a (CD79A, CD79a, immunoglobulin-associated alpha, a B-cell specific protein that covalently interacts with Ig beta (CD79B) and forms a complex on the surface with Ig M molecules, transduces a signal involved in B-cell differentiation, Genbank accession No. NP-001774.1);
(29) CXCR5 (Burkitt's lymphoma receptor 1, a G protein-coupled receptor that is activated by the CXCL13 chemokine, functions in lymphocyte migration and humoral defense, plays a role in HIV-2 infection and perhaps development of AIDS, lymphoma, myeloma, and leukemia, Genbank accession No. NP_001707.1);
(30) HLA-DOB (Beta subunit of MHC class II molecule (1a antigen) that binds peptides and presents them to CD4+ T lymphocytes, Genbank accession No. NP_002111.1);
(31) P2X5 (Purinergic receptor P2X ligand-gated ion channel 5, an ion channel gated by extracellular ATP, may be involved in synaptic transmission and neurogenesis, deficiency may contribute to the pathophysiology of idiopathic detrusor instability, Genbank accession No. NP_002552.2);
(32) CD72 (B-cell differentiation antigen CD72, Lyb-2, Genbank accession No. NP_001773.1);
(33) LY64 (lymphocyte antigen 64 (RP105), type I membrane protein of the leucine rich repeat (LRR) family, regulates B-cell activation and apoptosis, loss of function is associated with increased disease activity in patients with systemic lupus erythematosis, Genbank accession No. NP_005573.1);
(34) FcRH1 (Fc receptor-like protein 1, a putative receptor for the immunoglobulin Fc domain that contains C2 type (g-like and ITAM domains, may have a role in B-lymphocyte differentiation, Genbank accession No. NP_443170.1);
(35) IRTA2 (Immunoglobulin superfamily receptor translocation associated 2, a putative immunoreceptor with possible roles in B cell development and lymphomagenesis; deregulation of the gene by translocation occurs in some B-cell malignancies, Genbank accession No. NP_112571.1); and
(36) TENB2 (putative transmembrane proteoglycan, related to the EGF/heregulin family of growth factors and follistatin, Genbank accession No. AF179274).

As used herein, the terms "drag" or "D" refer to any compound possessing a desired biological activity and a reactive functional group that may be used to incorporate the drug into the conjugate of the invention. The desired biological activity includes the diagnosis, cure, mitigation, treatment, or prevention of disease in man or other animals. Thus, so long as it has the needed reactive functional group, the term "drug" refers to chemicals recognized as drugs in the official Chinese National Pharmacopeia, official United States Pharmacopeia, official Homeopathic Pharmacopeia of the United States, or official National Formulary, or any supplement thereof. Exemplary drugs are set forth in the Physician's Desk Reference (PDR) and in the Orange Book maintained by the U.S. Food and Drag Administration (FDA). New drugs are continually being discovered and developed, and the present invention provides that these new drugs may also be incorporated into a prodrug form of the present invention.

Preferably, the drug is: a cytotoxic drug useful in cancer therapy; a protein or polypeptide possessing a desired biological activity, such as a toxin, e.g., abrin, ricin A, pseudomonas exotoxin, and diphtheria toxin; other suitable proteins include tumor necrosis factor, α-interferon, β-interferon, nerve growth factor, platelet derived growth factor, tissue plasminogen activator, and biological response modifiers, for example, lymphokines, interleukin-1 (IL-1), interleukin-2 (IL-2), interleukin-6 (IL-6), granulocyte macrophage colony stimulating factor (GM-CSF), granulocyte colony stimulating factor (G-CSF), or other growth factors.

In one aspect, the drugs are maytansine and maytansinoids. Maytansine compounds inhibit cell proliferation by inhibiting the formation of microtubules of the microtubulin protein, tubulin (Temillard et al. 1975, Science 189:1002-1005; U.S. Pat. No. 5,208,020). Maytansinoids are derivatives of maytansine. Both maytansine and maytansinoids are highly cytotoxic, but their clinical use in cancer therapy has been greatly limited due to poor selectivity for tumors. However, the high cytotoxic potency enables them to be attractive drug moieties in ADCs. The structures shown below are maytansine, maytansinoids, and three representative maytansinoids mostly used in ADC drugs.

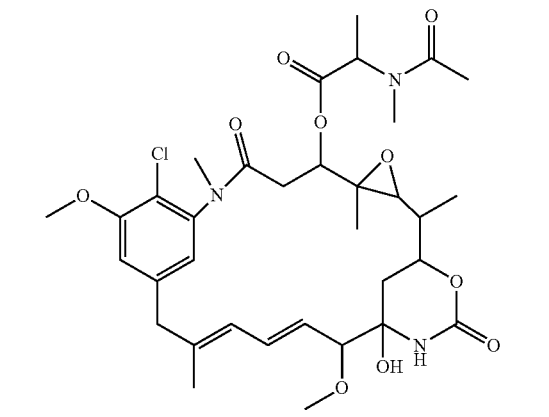

Maytansine

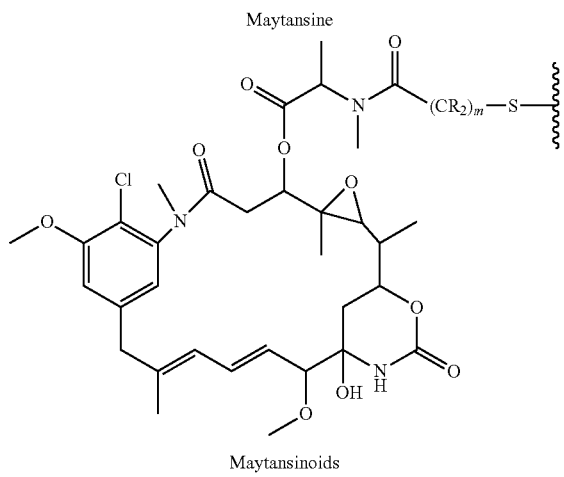

Maytansinoids

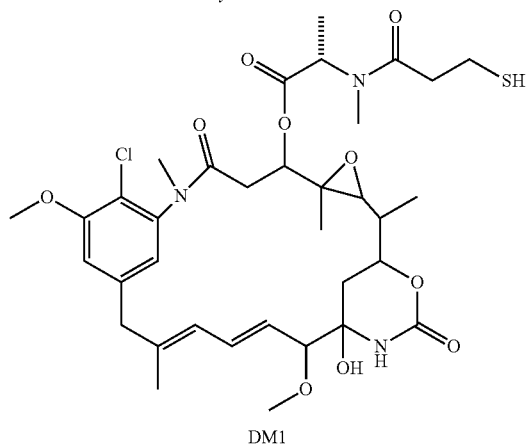

DM1

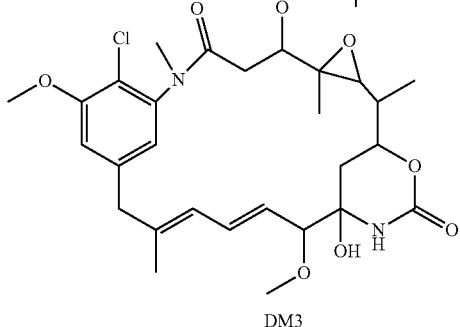

DM3

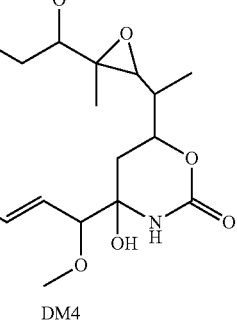

DM4

The key raw material for preparing maytansinoids is maytansinol, which is obtained from ansamitocins hydrolysis. Ansamitocins could be accessibly produced by fermentation. Ansamitocin derivatives (WO 2012/061590) and alaninyl maytansinol (US 2012/0121615) are also reported to be good candidates as ADC warheads (the structures of the two kinds of molecules are as represented by the following formulae).

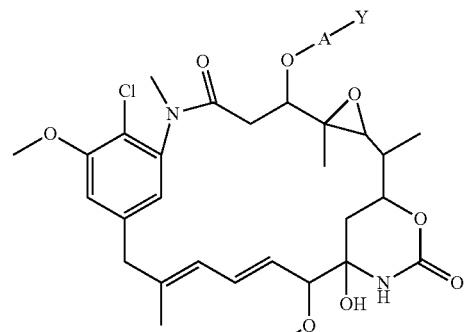

A is C=O, (C=O)NR', and (C=O)O
Y is a substituent group

Ansamitocin derivatives

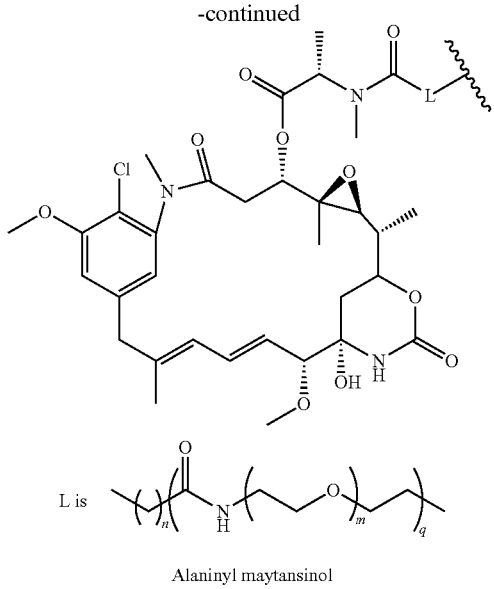

L is

Alaninyl maytansinol

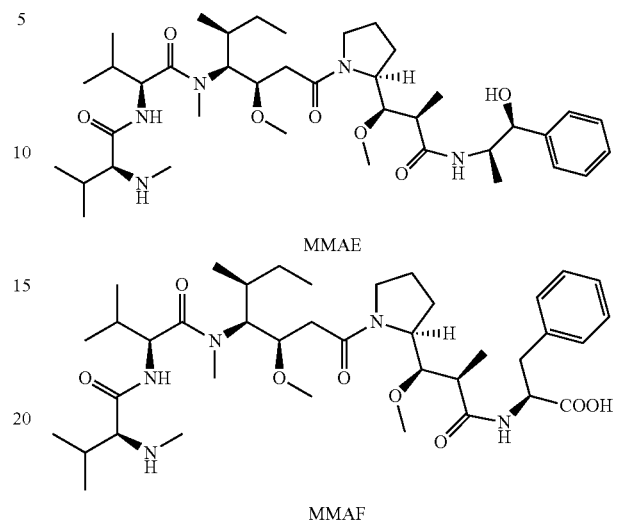

MMAE

MMAF

In one aspect, the drugs are Auristatins. Auristatins are synthetic analogues of Dolastatin 10, which was isolated from the marine mollusk *Dolabella auricularia* and found to have biological activity (U.S. Pat. No. 7,498,298). Dolastatin 10 is an agent that inhibits tubulin polymerization by binding to the same domain on tubulin as the anticancer drug vincristine. Dolastitin 10, auristatin PE, and auristatin E are linear peptides having four amino acids, three of which are unique to the dolastatin class of compounds, and a C-terminal amide. Two representative auristatins, monomethyl auristatin E (MMAE) and monomethyl auristatin F (MMAF), are preferred drug moiety candidates for ADCs.

In one aspect, the drugs are calicheamicins. Calicheamicins are antitumor antibiotics that bind to the minor groove of DNA and produce site-specific double-strand DNA breaks, causing cell death. Calicheamicins are potent at sub-picomolar concentrations in vitro, but their low therapeutic index precluded further development clinically. The high potency, however, makes them good candidates for ADCs (for example, Gemtuzumab Ozogamicin and Inotuzumab Ozogamicin).

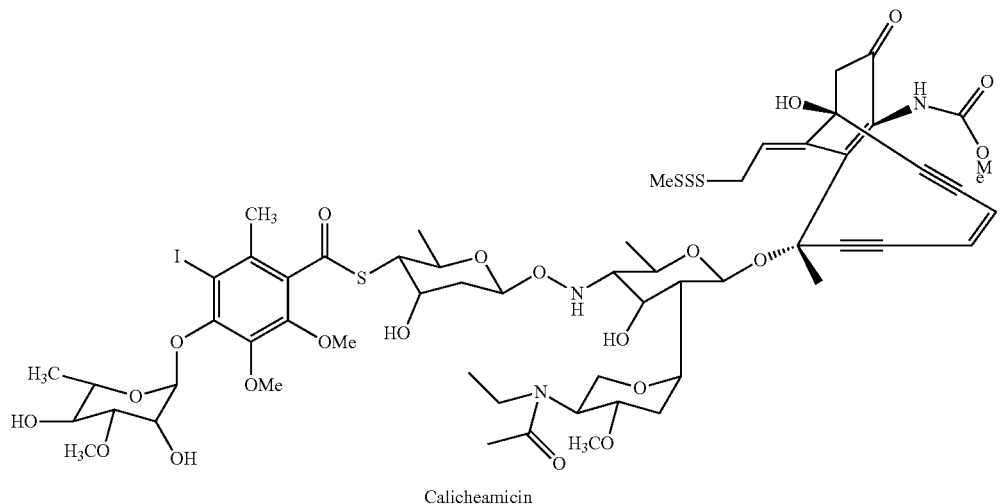

Calicheamicin

In one aspect, the drags are doxorubicins. Doxorubicin is an intercalating agent that blocks DNA replication and is used as chemotherapeutic agent. Due to the relative low potency of doxorubicin ($IC_{50}$ of 0.1-0.2 μM for human carcinoma lines, whereas subnanomolar activities are now typically seen for ADC payloads), application of doxorubicin as ADC drug moiety is not popular.

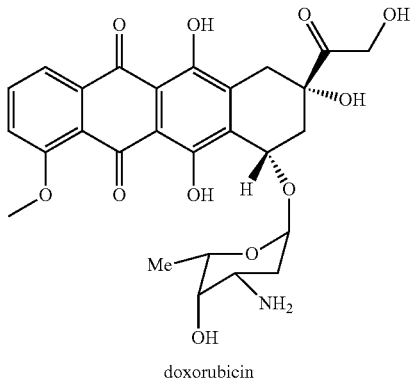 [SMILES: COc1cccc2c1C(=O)c1c(O)c3c(c(O)c1C2=O)C[C@@](O)(C(=O)CO)C[C@@H]3OC1CC(N)C(O)C(C)O1]

doxorubicin

In one aspect, the drags are duocarmycins, CC-1065 and other cyclopropapyrroloind-4-one (CPI) derivatives, which are potent minor-groove binding DNA alkylating agents. Cyclopropabenzindol-4-one analogues (CBI) are chemically more stable, biologically more potent, and synthetic ally more accessible than their parent compounds incorporating the natural CPI alkylating subunit. One representative CBI derivative is the phenolic hydroxyl group-protected CBI (see the following formula), which has decreased prodrug toxicity and improved water solubility.

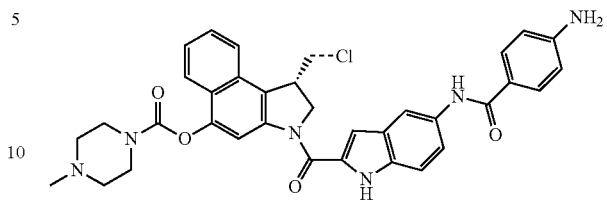

In one aspect, the drags are pyrrolo[2,1-c][1,4]benzodiazepines (PBDs) or PBD dimers. The pyrrolo[2,1-c][1,4] benzodiazepines (PBDs) are a family of natural products produced by *Streptomyces* species with the unique characteristic of forming nondistortive covalent adducts in the minor groove of DNA specifically at purine-guanine-purine sequences. There is growing interest in using PBDs as part, of a small-molecule strategy for targeting DNA sequences and also as novel anticancer and antibacterial agents. (Antonow et al. 2008, Biochemistry 47: 11818-11829). The biological activity of these molecules can be potentiated by joining two PBD units together through their C8/C8'-hydroxyl functionalities via a flexible alkylene linker (WO 2011/130616). The PBD dimers are thought to form sequence-selective DNA lesions such as the palindromic 5'-Pu-GATC-Py-3' interstrand cross-link, which mainly accounts for their biological activity. These compounds have been shown to be highly useful cytotoxic agents and good candidates as ADC warheads.

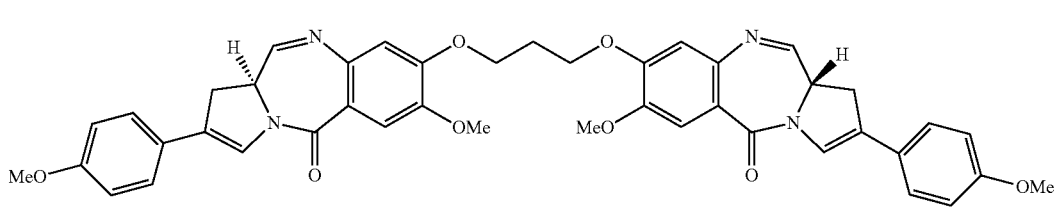

SG2201

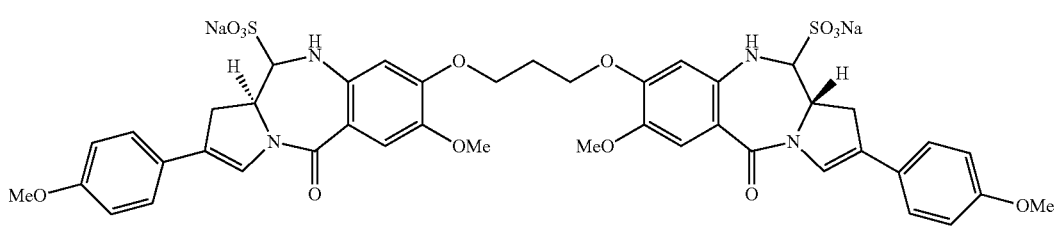

SG2285

In another aspect, the drugs are not limited to above-mentioned categories and include all that could be used in ADCs.

According to drug release mechanism in cells, as used herein, the terms "linkers" or "ADC linkers" could be divided into two types: noncleavable and cleavable linkers.

For ADCs with noncleavable linkers, the release mechanism is believed to occur via internalization of the ADC followed by degradation of the mAb component in the lysosome, resulting in the release of the small molecular drug still attached via the linker to an antibody amino acid residue. The chemical modification of the drug didn't diminish its cytotoxic potential. This form of the drug is, however, charged (amino-acid residue) and presumably not able to diffuse into neighboring cells. Hence, it can't kill adjacent tumor cells (bystander effects) that don't express the target antigen (antigen-negative cells) (Ducry et al. 2010, Bioconjugate Chem. 21: 5-13).

Cleavable linkers, as the name implies, could be cleaved within the target cells that release the active drugs (small molecule drugs themselves). Cleavable linkers can be categorized into two main groups: chemically labile and enzyme-labile linkers.

Chemically labile linkers could be selectively cleaved upon the differential properties between the plasma and some cytoplasmic compartments. Such properties include pH value, glutathione concentration, etc.

For pH sensitive linkers, generally called acid-cleavable linker, the linkers are relatively stable in the blood's neutral environment (pH 7.3-7.5), but will undergo hydrolysis in the mildly acidic endosomes (pH 5.0-6.5) and lysosomes (pH 4.5-5.0). First generation of ADCs mostly used these kinds of linkers, like hydrozones, carbonate, acetal, ketal. However, due to the limited plasma stability of the acid-cleavable linkers, the ADCs based on these linkers have relatively short half-life (2-3 days). The low half-lives, to a certain degree, preclude the application of pH-sensitive linkers in the new generations of ADCs.

For glutathione-sensitive linkers, generally called disulfide linkers, the release is attributed to the high intracellular concentration of glutathione in the cytoplasma (millimolar range) compared to the relatively low concentration in the blood (micromolar range). This is especially true for tumor cells, where the hypoxic state results in enhanced activity of reductive enzymes and therefore even higher glutathione concentrations. Disulfide bonds are thermodynamically stable and thus provide good stability in plasma.

Enzyme-labile linkers, such as peptide linkers, are alternative approaches to achieve better control of the drug release. The peptide linkage will be effectively cleaved by lysosomal proteases, like Cathepsin B or plasmin, present at elevated levels in certain tumor tissues. The peptidic linkages are deemed stable when circulating in plasma, as proteases are normally not active outside cells because of unfavorable pH and inhibition from serum protease inhibitors. Due to the high plasma stability and good intracellular cleaving selectivity and efficiency, enzyme-labile linkers are broadly selected as cleavable linker candidates in ADCs. Typical enzyme-labile linkers include Val-Cit (vc), Phe-Lys, etc.

Self-immolative linker is generally sited between cleavable linker and cytotoxic drug, or itself is part of cleavable linker. The working mechanism for self-immolative linker is that it can undergo self-structural rearrangement to release the active drug when the cleavable linker was cut by protease. General self-immolative linkers include p-aminobenzyl alcohol (PAB) and β-glucuronide, etc.

Antibody Drug Conjugates

The antibody drug conjugates provided in this invention are composed of antibody, tridentate linker, linker, and drug. Linker is referred to cleavable linker and non-cleavable linker.

Antibodies are comprised of globular proteins, which have an array of amino acids that have potential linkage sites for drug conjugation. Due to their tertiary and quaternary structure, only solvent-accessible amino acids will be conjugatable. In fact, high-yielding conjugations to antibodies occur through the ε-amino group of lysine residues or through the sulfhydryl group of cysteine residues.

The abundance of lysine side-chains at the protein surface gives multiple linkage sites for payload conjugation, which leads to a mixture of ADCs with different payload numbers (DARs) and conjugation sites.

The conjugation products provided by the invention, albeit still mixture, contain much narrower DAR-spanned products, compared to antibody drug conjugates produced traditionally. The average DAR thus obtained is close to 4, within an optimized ADC DAR range of 2-4. In addition, the conjugation products don't contain naked antibody (DAR=0), which have zero payload and thus ineffective for the cell killing. Also, the conjugation products don't contain heavily conjugated antibody (DAR=8), which clears more rapidly than those with low DAR numbers. As a result, the ADC products provided in this invention showed much improved homogeneity.

For tridentate linkers, the distance between two maleimide groups (linker size) may affect the interchain crosslinking between tridentate linkers and antibodies. The inventor synthesized a series of tridentate linkers of different size, together with the simplified form of tridentate linkers (bidentate linkers not containing drug-linking branches). To discover the effects of linker size on antibody interchain crosslinking, the conjugation products between these linkers and reduced antibodies were analyzed by SDS-PAGE and HIC.

Tridentate Linkers and Bidentate Linkers

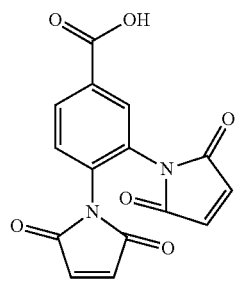

1

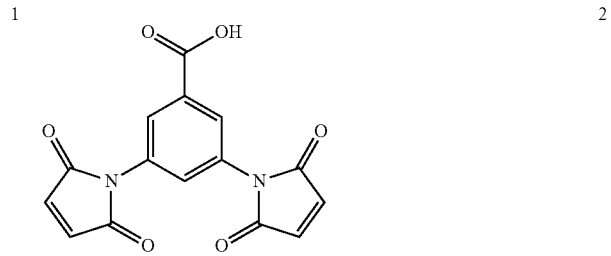

2

-continued
3
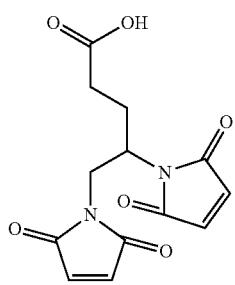
4
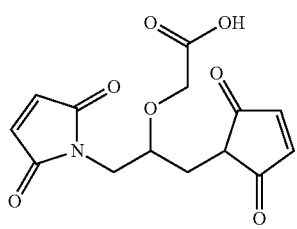
5
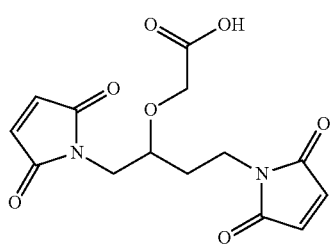
6
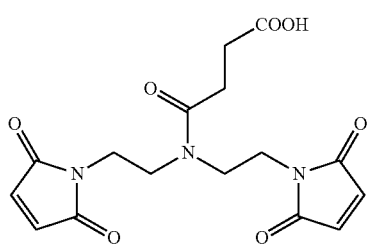
7
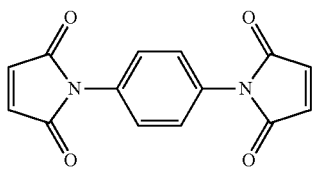
8
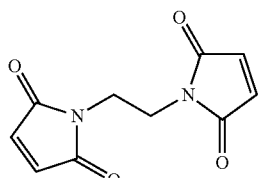
9
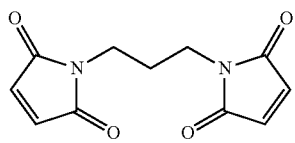
Antibody Drug Conjugates
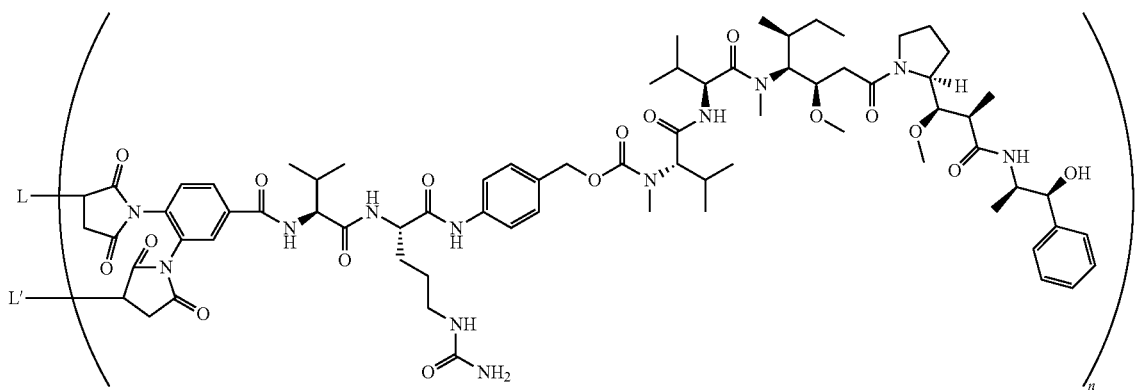
H-1-vcMMAE -continued
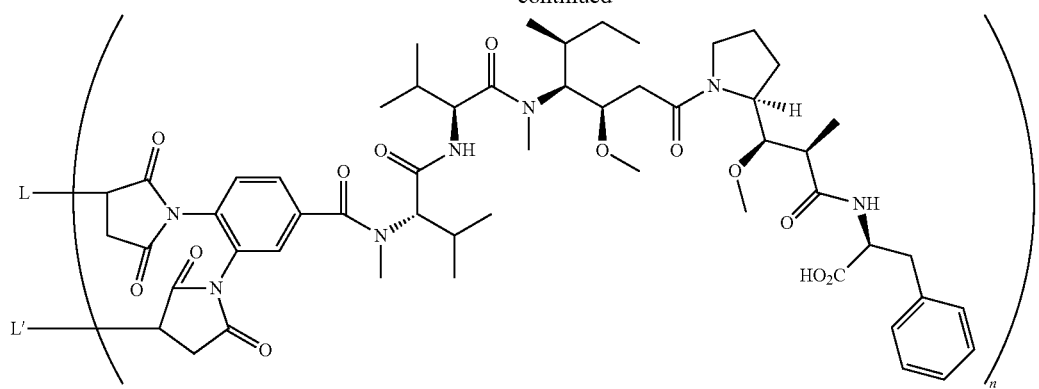
H-1-MMAF
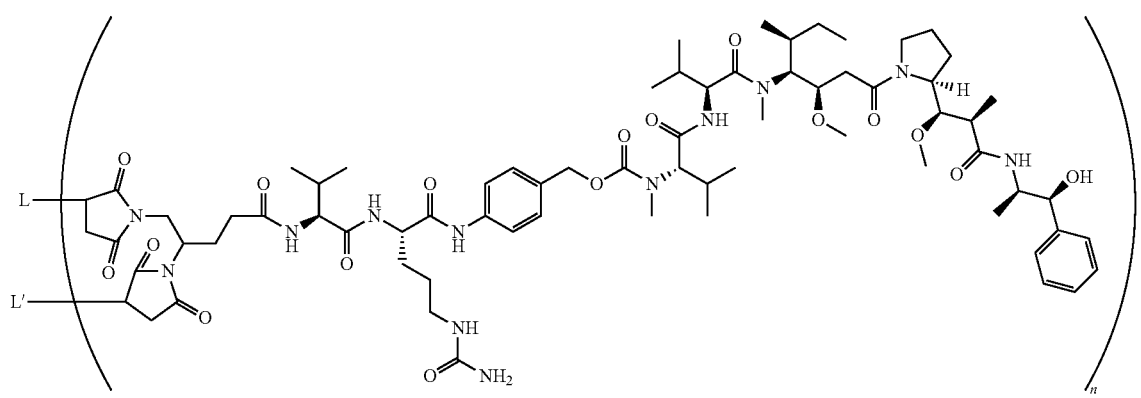
H-3-vcMMAE
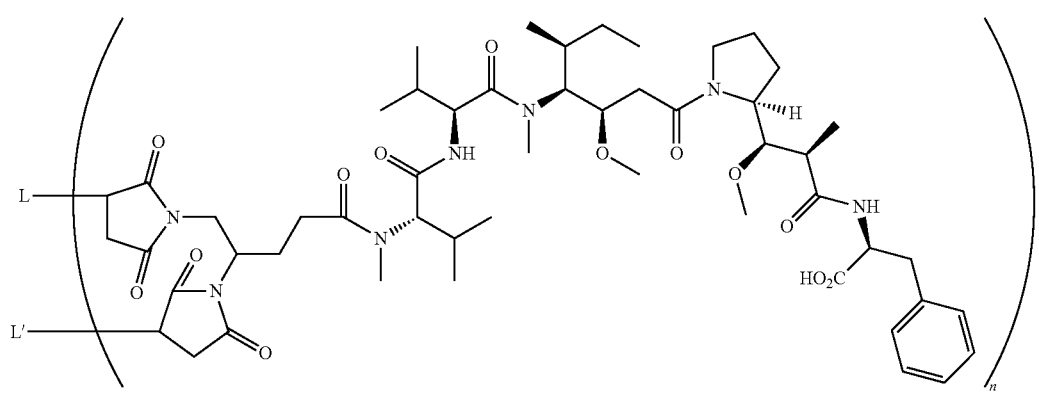
H-3-MMAF
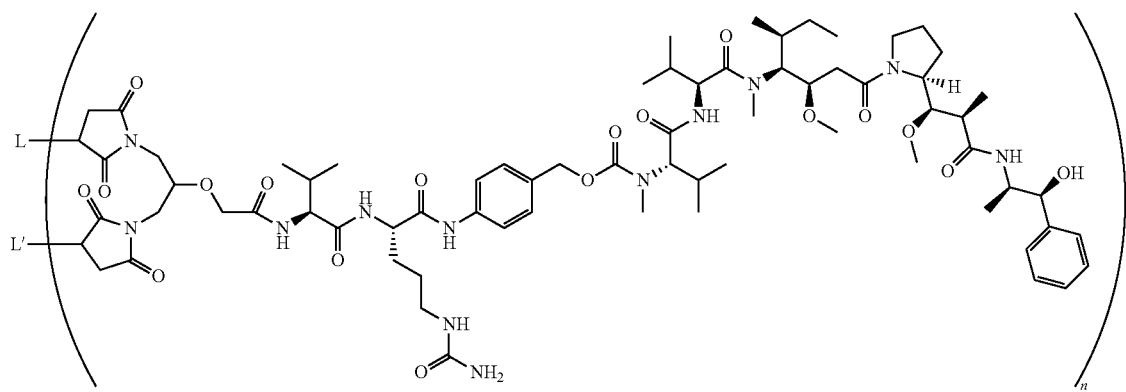
H-4-vcMMAE -continued

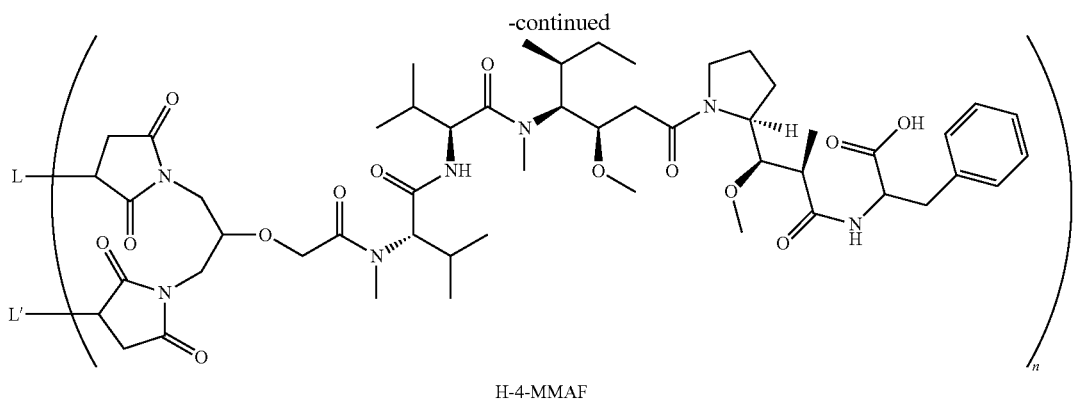

H-4-MMAF

Preparation Method

The conjugation procedure is shown in below scheme. In step A, a linker (L) and a tridentate linker (T) were conjugated to afford a tridentate linker-linker (T-L). In step B, T-L and a drug (D) were conjugated to give tridentate linker-linker-drug (T-LD). In step C, antibody inter-chain disulfide bonds were selectively reduced to produce a total of eight sulfhydryl groups. In step D, T-LD crosslinked the two adjacent sulfhydryl groups to afford partial/full inter-chain crosslinked ADCs.

The present invention provides compositions comprising an effective amount of a drug conjugate and a pharmaceutically acceptable carrier or vehicle.

The present invention provides methods for treatment of cancers or other tumors in animal subjects. The methods provide an effective amount of a drug conjugate composition to an animal subject with cancers or other tumors.

The present invention provides methods for treatment of autoimmune disease or infectious disease. The methods

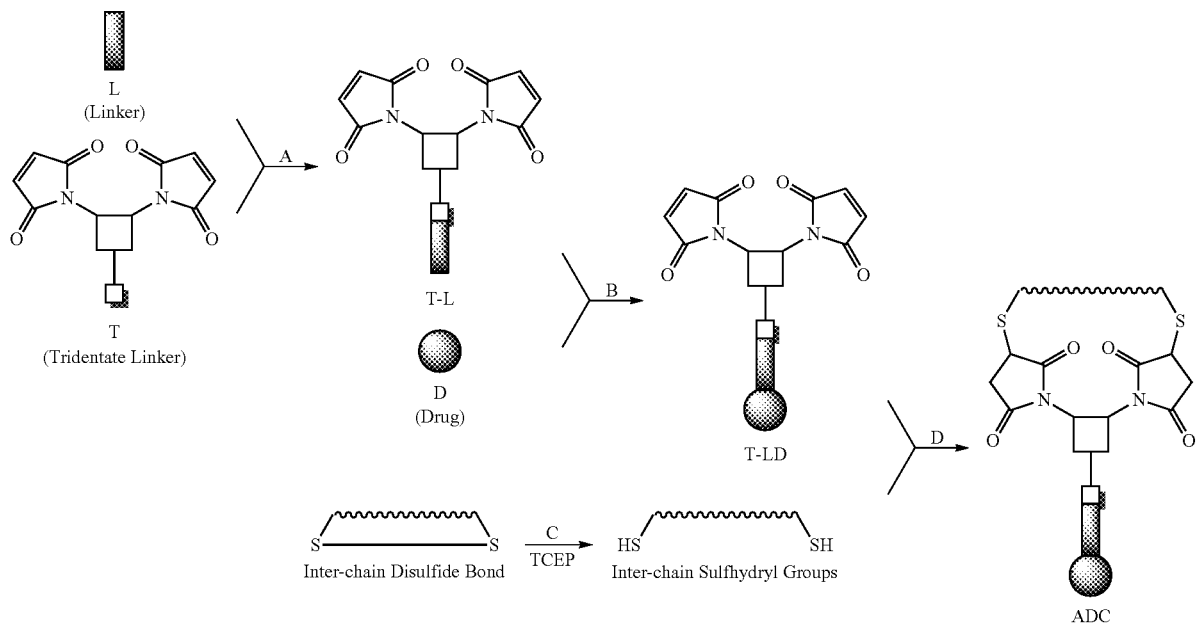

Uses

The present invention provides antibody drug conjugates that target a special cell population, bind to specific cell surface proteins (antigens), internalize with antigen, and release the drugs in active forms within the cell.

The present invention provides antibody drug conjugates that target a special cell population, bind to the specific ceil surface proteins (antigens), and take effects; or release drugs outside the cell, followed by the diffusion of the drugs into cell and taking effects.

provide an effective amount of a drug conjugate composition to an animal subject with autoimmune disease or infectious disease.

The above features provided by the present invention, or features provided by examples, can be combined at will. All features provided by the present invention can be applied together with any combination, and each feature can be substituted by any identical, equal, or similar feature. Except for special illustration, all disclosed features are only general examples of the equal or similar features.

The present invention has the main advantages as shown below.
1. The present invention provides coupling methods applicable to most antibodies, which in turn can avoid complicated antibody engineering used to introduce specific sites for coupling. The coupling methods may have very broad application prospect.
2. The present invention provides innovative tridentate linkers that can couple antibodies via simple chemical method. Although the antibody drug conjugates prepared via this method are not fully homogeneous, the conjugates has much narrower DAR distribution, compared to those prepared by traditional coupling methods. As a result, the homogeneity of the ADC products is greatly improved.

The present invention is further elaborated by examples. It should be understood that these examples are used to illustrate the present invention, while not limit its scope. The unstated experiment conditions are generally according to routine conditions or conditions suggested by manufacturers. Unless otherwise stated, all percentage, ratio, proportion, or amount are calculated by weight.

The % w/v unit used in the present invention is well known in the art. For example, it means the solute weight in 100 mL of solution.

Unless otherwise defined, all professional and scientific terms used in the present invention have the same meaning as those familiar by the expertise in the art. Furthermore, any method or material similar or equal to those used in the present invention can be applied herein. The optimized methods and materials used in the present invention are only used for illustration while not for limitation.

The general procedures used in the present invention are described below.

General Procedure A

Synthesis of Tridentate Linkers

The synthesis of tridentate linkers could be referred to synthesis of bismaleimides (Girouard et al. 2005, J. Am. Chem. Soc. 127: 559-566).

General Procedure B

Preparation of Antibody Linker Conjugates and Antibody Drug Conjugates

TCEP (10 eq, stock solution 10 mM) was added to a solution of antibody (2-10 mg/mL, 25 mM borate buffer, containing 25 mM NaCl and 1 mM DTP A, pH 8.0). The reaction mixture was incubated at 37° C. in a shaker for 1 h, and then cooled to ~10° C.

To the above solution of reduced antibody cooled at 10° C. was added DMSO and 5-100 equivalent bid en tate/tri dentate linker or tridentate linker-(linker)-drug (stock solution in DMSO), and the % v/v of DMSO was controlled at ~15%. The conjugation reaction was incubated at 10° C. for 1 h.

Excess cysteine solution was added to the reaction mixture to quench the unreacted bidentate/tridentate linker or tridentate linker-(linker)-drug. The quenching reaction was kept at 10° C. for 30 min. The reaction mixture was ultrafiltered to remove excess cysteine, bidentate/tridentate linker-cysteine addicts or tridentate linker-(linker)-drug-cysteine adducts. The residue solution was sterile filtered through 0.2 µm filter, and kept at 4° C.

General Procedure C

SDS-PAGE Analysis

SDS-PAGE was measured on Bio-Rad 165-8001 electrophoresis instrument. A sample (≤10 µg by weight) was combined with the corresponding sampling buffer, and the mixture was heated in a boiling water bath for 1 min. The sample and standard protein (5 µL/hole) were added to the spacer gel comb holes sequentially, and the electrophoresis was conducted at 220 V for 45 min. The gel was rinsed by deionized water, and stained in coomassie light blue solution G250 on a shaker for 16 h. The stained gel was rinsed by deionized water for three times, and destained on a shaker for 2 h. The destained gel was transferred to an imager to record the gel image.

General Procedure D

Hydrophobic Interaction Chromatography (HIC) Analysis

HIC was measured on an Agilent 1100 instrument. The column is TSKgel butyl-NPR column (4.6×35 mm, 2.5 µm, Tosoh Bioscience, Shanghai). The method consisted of a linear gradient from 100% buffer A [50 mM potassium phosphate, 1.5 M ammonium sulfate, pH 7.0] to 100% buffer B [80% v/v 50 mM sodium phosphate, pH 7.0, 20% v/v isopropanol] in 25 minutes. The flow rate was set at 0.8 mL/min, the temperature was set at 30° C., and detection was followed at both 230 and 280 nm.

General Procedure E

Enzyme-Linked Immunosorbent Assay (ELISA)

Indirect ELISA was used to analyze binding ability of the antibody or antibody-drug conjugate to the corresponding antigen. The Her2 antigen was immobilized on a solid-phase support (96 well microplate) by coating, and then unbound antigen was removed by washing. Serial dilutions of test antibody or antibody-drug conjugate were added, wherein specific antibody or antibody-drug conjugate bound to the antigen and formed solid-phase antigen-antibody complexes. The unbound antibody or antibody-drug conjugate was removed by washing. The enzyme labeled anti-antibody was added to bind to the antibody or antibody-drug conjugate bound to the antigen. The unbound anti-antibody was removed by washing. After washing, substrate solution was added to develop color, and the optical density was read by a microplate reader at 450 nm/630 nm, based on which the $EC_{50}$ was calculated.

General Procedure F

Cell Proliferation Assay

Generally, the cytotoxic or cytostatic activity of an antibody-drug conjugate is measured by: exposing mammalian cells having tumor-associated antigens or receptor proteins to the antibody or the ADC in a cell culture medium; culturing the cells for a period from about 2 to 5 days; and measuring cell viability. Cell-based in vitro assays were used to measure viability, i.e. proliferation ($IC_{50}$), cytotoxicity ($EC_{50}$), and induction of apoptosis (caspase activation) of the ADC.

Unless otherwise stated, all anhydrous solvents were purchased from the suppliers and kept under nitrogen. All other reagents and solvents were purchased at high purity and not purified before use.

$^1$H NMR spectrum was collected on a Bruker Avance III 500 MHz instrument. Chemical shift (δ) unit is ppm, and the reference reagent is TMS (δ=0). The coupling constant (J) unit is Hz.

Low resolution mass spectrum was collected on Agilent 6110 (acid method) and 6120B (base method) mass spectrometers coupled with Agilent 1200 HPLC. The acid HPLC method uses Waters Sunfire C18 reverse phase column (4.60×50 mm, 3.5 μm) for separation, and the eluting gradient is 5%-95% B (acetonitrile, containing 0.01% TFA) in A (water, containing 0.01% TFA) in 1.4 min. The base HPLC method used Waters Xbridge C18 reverse phase column (4.60×50 mm, 3.5 μm), and the eluting gradient is 5%-95% B (acetonitrile) in A (water, containing 10 mM ammonium bicarbonate) in 1.5 min. The flow rate is 2.0 mL/min, and the column temperature is 40° C.

Purification by preparative HPLC was conducted on a Gilson instrument. Waters Sunfire C18 reverse phase column (250×19 mm, 10 μm) was used for separation, and the sample was eluted by water (containing 0.1% TFA)-acetonitrile gradient eluent.

SK-BR-3 human breast cancer cell was purchased from ATCC. Her2 antigen was purchased from Sino Biological Inc. The enzyme labeled anti-antibody was purchased from Sigma (Shanghai). Substrate solution was purchased from Decent Biotech (Shanghai). Cell Counting Kit (CCK-8) cell proliferation and cytotoxicity assay kit was purchased from Dojindo (Shanghai).

Example 1

Preparation of Compound 1

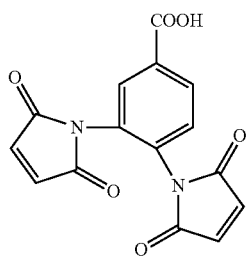 [SMILES: O=C(O)c1ccc(N2C(=O)C=CC2=O)c(N2C(=O)C=CC2=O)c1]

A solution of 3,4-diaminobenzoic acid (1.5 g, 9.87 mmol) and maleic anhydride (2.9 g, 29.6 mmol) in chloroform (90 mL) was refluxed for 20 h. After cooling to room temperature, the yellow precipitate was collected by filtration. The solid was resuspended in acetic anhydride (75 mL), to which sodium acetate (324 mg, 3.95 mmol) was added. The reaction mixture was stirred at 100° C. for 2 h, and then poured onto ice, followed by the addition of 150 mL of cold water. The mixture was stirred fiercely for 30 min, and volatile solvent was removed by rotavap. The residue was extracted by ethyl acetate, and the organic phase was dried over anhydrous sodium sulfate, filtered, and concentrated. Recrystallization in acetonitrile afforded white solid (280 mg). LC-MS m/z (ES$^+$), 313.1 (M+H)$^+$; $^1$H NMR (DMSG-d$_6$) δ8.11; (dd, 1H), 8.02; (d, 1H), 7.59; (d, 1H), 7.19; (s, 2H), 7.16; (s, 2H).

Example 2

Preparation of Compound 2, 7, 8, and 9

The preparation of compound 2, 7, 8, and 9 followed the methods in literature (General Procedure A).

Example 3

Preparation of Compound 10

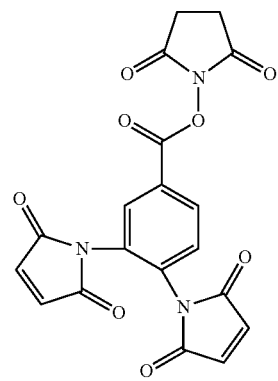 [SMILES: O=C(ON1C(=O)CCC1=O)c1ccc(N2C(=O)C=CC2=O)c(N2C(=O)C=CC2=O)c1]

To a suspension of compound 1 (62 mg, 0.20 mmol) in dry THE (10 mL) cooled at 0° C. was added N-hydroxysuccinimide (24 mg, 0.21 mmol) and a solution of DCC (50 mg, 0.24 mmol) in THF (2 mL). The reaction mixture was stirred at 0° C. for 2 h, and then warmed to 25° C. and stirred for 12 h. The mixture was filtered at 0° C. to remove the solid, and the filtrate was concentrated to give a white solid (60 mg). The crude product was used for next step without further purification. LC-MS m/z (ES$^+$), 427.2 (M+NH$_4$)$^+$.

Example 4

Preparation of Compound 11

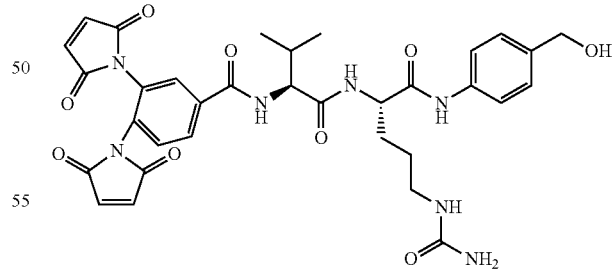

To s solution of compound 10 (50 mg, 0.12 mmol) in DMF (2 mL) was added Val-Cit-PABOH (TEA salt, 80 mg, 0.16 mmol; Bioconjugate Chem. 2002, 13, 855-869) and N,N-diisopropylethylamine (DEEA, 28 μL, 0.16 mmol). The reaction mixture was stirred at room temperature for 3 h. Solvent was removed by rotavap, and the residue was purified by preparative HPLC to give a while solid (37 mg). LC-MS m/z (ES$^+$), 674.3 (M+H)$^+$.

Example 5

Preparation of Compound 12

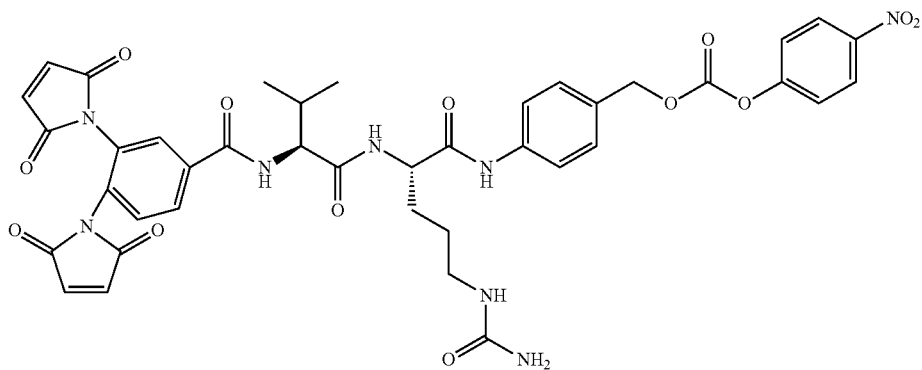 [SMILES: CC(C)[C@H](NC(=O)c1ccc(N2C(=O)C=CC2=O)c(N2C(=O)C=CC2=O)c1)C(=O)N[C@@H](CCCNC(N)=O)C(=O)Nc1ccc(COC(=O)Oc2ccc([N+](=O)[O-])cc2)cc1]

To a solution of compound 11 (37 mg, 55 μmol) in DMF (2 mL) was added bis(4-nitrophenyl) carbonate (33 mg, 110 μmol) and DIEA (14 μL, 82 μmol). The reaction mixture was stirred at room temperature for 5 h, and solvent was removed by rotavap. The oily residue was triturated with ethyl acetate (2 mL) to give a precipitate, and further triturated with diethyl ether (10 mL). The precipitate was collected by filtration and dried to give a pale yellow solid (43 mg). LC-MS m/z (ES$^+$), 839.3 (M+H)$^+$.

Example 6

Preparation of Compound 13

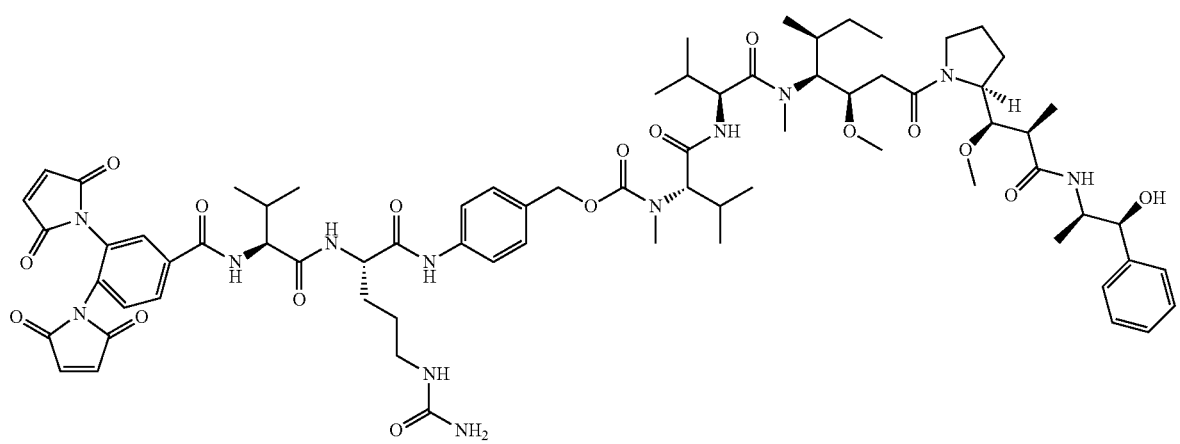 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(NC(=O)[C@H](CCCNC(N)=O)NC(=O)[C@@H](NC(=O)c2ccc(N3C(=O)C=CC3=O)c(N3C(=O)C=CC3=O)c2)C(C)C)cc1)C(C)C]

Compound 12 (35 mg, 42 μmol), MMAE (30 mg, 42 μmol; U.S. Pat. No. 6,884,869) and N-hydroxybenzotriazole (HOBt, 1.2 mg, 8.0 μmol) was added successively to dry DMF (2 mL) and pyridine (0.4 mL). The reaction mixture was stirred at room temperature for 30 min, and solvent was removed in vacuo. The residue was purified by preparative HPLC to give white powder (12 mg). LC-MS m/z (ES$^+$), 1417.7 (M+H)$^+$.

Example 7

Preparation of Compound 14

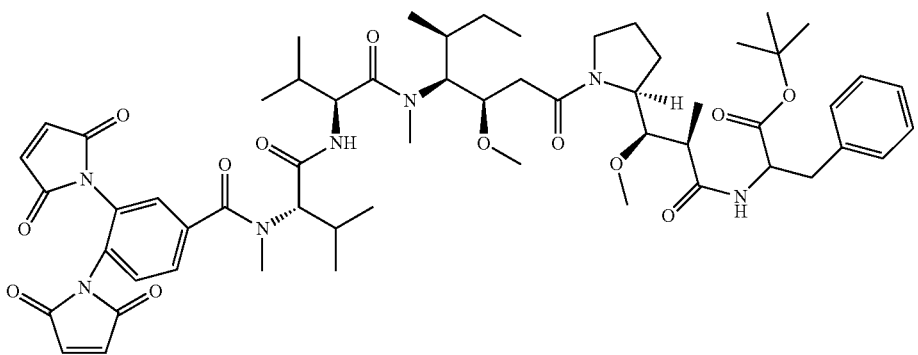 [SMILES: CC[C@H](C)[C@@H]([C@@H](CC(=O)N1CCC[C@H]1[C@H](OC)[C@@H](C)C(=O)NC(Cc1ccccc1)C(=O)OC(C)(C)C)OC)N(C)C(=O)[C@@H](NC(=O)[C@H](C(C)C)N(C)C(=O)c1ccc(N2C(=O)C=CC2=O)c(N2C(=O)C=CC2=O)c1)C(C)C]

To a solution of compound 1 (28 mg, 90 μmol), MMAF-O-t-Bu (45 mg, 57 μmol, U.S. Pat. No. 7,964,567) and DIEA (31 μL, 0.18 mmol) in DCM (3 mL) was added 2-(7-aza-1H-benzotriazole-1-yl)-1,1,3,3-tetramethyluronium hexafluorophosphate (HATU, 34 mg, 90 μmol). The reaction mixture was stirred at room temperature under N$_2$ for 3 h. Solvent was removed in vacuo, and the residue was purified by column chromatography (silica gel, DCM/MeOH 40/1) to give colorless oil (50 mg). LC-MS m/z (ES$^+$), 1083.7 (M+H)$^+$.

Example 8

Preparation of Compound 15

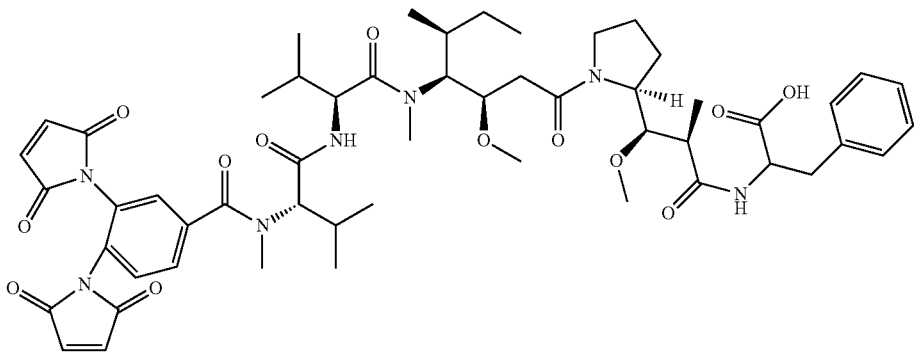 [SMILES: CC[C@H](C)[C@@H]([C@@H](CC(=O)N1CCC[C@H]1[C@H](OC)[C@@H](C)C(=O)NC(Cc1ccccc1)C(=O)O)OC)N(C)C(=O)[C@@H](NC(=O)[C@H](C(C)C)N(C)C(=O)c1ccc(N2C(=O)C=CC2=O)c(N2C(=O)C=CC2=O)c1)C(C)C]

To a solution of compound 14 (50 mg, 46 μmol) in DCM (3 mL) cooled at 0° C. was added trifluoroacetic acid (TFA, 1 mL). The reaction mixture was stirred at room temperature for 8 h. Solvent was removed in vacuo, and the residue was purified by preparative HPLC to give a white solid (13 mg). LC-MS m/z (ES$^+$), 1026.5 (M+H)$^+$.

Example 9

Preparation of Compound 16

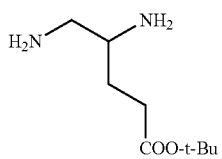

To a solution of (S)-4,5-diaminopentanoic acid dihydrochloride (205 mg, 1 mmol) in tert-butyl acetate (16 mL) was added perchloric acid (0.22 mL). The reaction mixture was stirred at room temperature for 22 h. Sodium bicarbonate (0.84 g, 10 mmol) was added to quench the reaction, and solvent was removed in high vacuum (avoid high temperature). The oily residue was triturated with chloroform and diethyl ether to give a precipitate. The solid was collected by filtration and dried in high vacuum to give moisture-sensitive gray solid (75 mg).

Example 10

Preparation of Compound 17

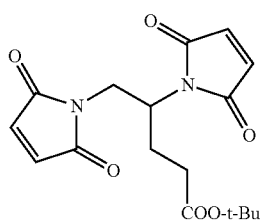

Compound 16 (75 mg, 0.4 mmol) and maleic anhydride (86 mg, 0.88 mmol) was added successively into DMF (5 mL), and the mixture was stirred at room temperature for 16 h. Acetic anhydride (5 mL), triethylamine (TEA, 167 μL, 1.2 mmol) and nickel acetate tetrahydrate (catalytic) were added, and the reaction mixture was stirred at 90° C. for 2 h. Volatile solvent was removed in vacuo, and the product was extracted with ethyl acetate. The organic phase was washed with saturated sodium carbonate, brine, dried over anhydrous sodium sulfate, and concentrated. The residue was purified by column chromatography (silica gel, petroleum ether/ethyl acetate 4/1) to give colorless oil (33 mg). LC-MS m/z (ES$^+$), 366.3; (M+NH$_4$)$^+$; $^1$H NMR (CDCl$_3$) δ6.65; (s, 2H), 6.64; (s, 2H), 4.21-4.18; (m, 1H), 4.05; (dd, 1H), 3.67; (dd, 1H), 2.41-2.37; (m, 1H), 2.24-2.13; (m, 2H), 2.11-2.05; (m, 1H), 1.43; (s, 9H).

Example 11

Preparation of Compound 3

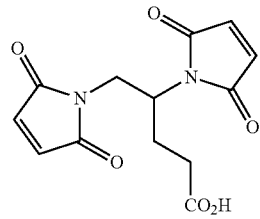 [SMILES: O=C(O)CCC(CN1C(=O)C=CC1=O)N1C(=O)C=CC1=O]

To a solution of compound 17 (80 mg, 0.43 mmol) in DCM (6 mL) was added TFA (3 mL). The reaction mixture was stirred at room temperature for 3 h and concentrated. The residue was purified by preparative HPLC to give a white solid (41 mg). LC-MS m/z (ES$^+$), 291.0 (M−H)$^{+/}$; $^1$H NMR (CDCl$_3$) δ6.67; (s, 4H), 4.23-4.18; (m, 1H), 4.04; (dd, 1H), 3.69; (dd, 1H), 2.49-2.42; (m, 1H), 2.34; (t, 2H), 2.15-2.09; (m, 1H).

Example 12

Preparation of Compound 18

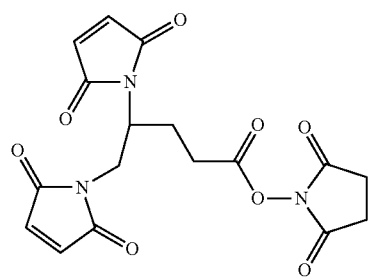 [SMILES: O=C(CCC(CN1C(=O)C=CC1=O)N1C(=O)C=CC1=O)ON1C(=O)CCC1=O]

Compound 18 was prepared from compound 3, via the similar synthetic procedure as Example 3. LC-MS m/z (ES$^+$). 389.8 (M+H)$^+$.

Example 13

Preparation of Compound 19

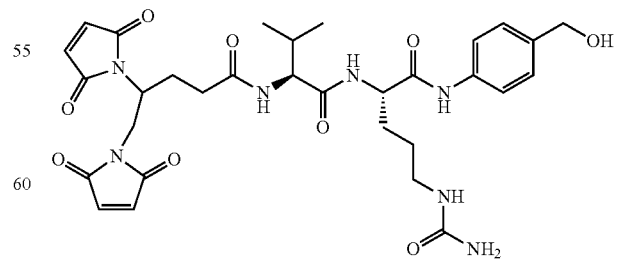

Compound 19 was prepared from compound 18, via the similar synthetic procedure as Example 4. LC-MS m/z (ES$^+$), 654.8 (M+H)$^+$.

Example 14
Preparation of Compound 20
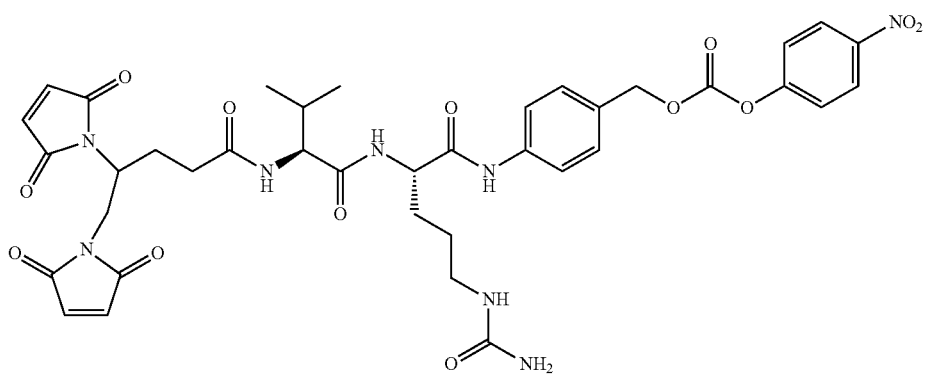 [SMILES: CC(C)[C@H](NC(=O)CCC(CN1C(=O)C=CC1=O)N1C(=O)C=CC1=O)C(=O)N[C@@H](CCCNC(N)=O)C(=O)Nc1ccc(COC(=O)Oc2ccc([N+](=O)[O-])cc2)cc1]
Compound 20 was prepared from compound 19, via the similar synthetic procedure as Example 5. LC-MS m/z (ES$^+$), 819.3 (M+H)$^+$.
Example 15
Preparation of Compound 21
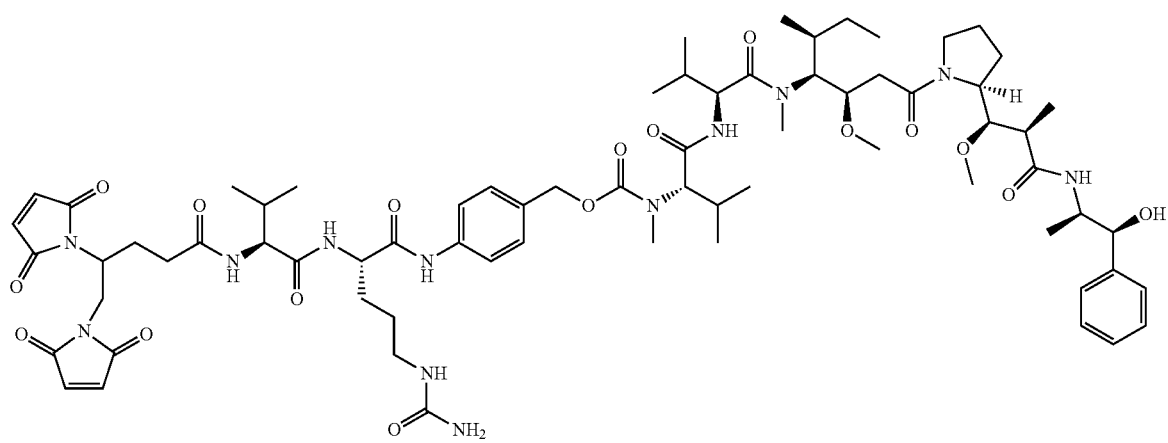 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(NC(=O)[C@H](CCCNC(N)=O)NC(=O)[C@@H](NC(=O)CCC(CN2C(=O)C=CC2=O)N2C(=O)C=CC2=O)C(C)C)cc1)C(C)C]

Compound 21 was prepared from compound 20, via the similar synthetic procedure as Example 6. LC-MS m/z (ES⁺), 1397.7 (M+H)⁺.

Example 16

Preparation of Compound 22

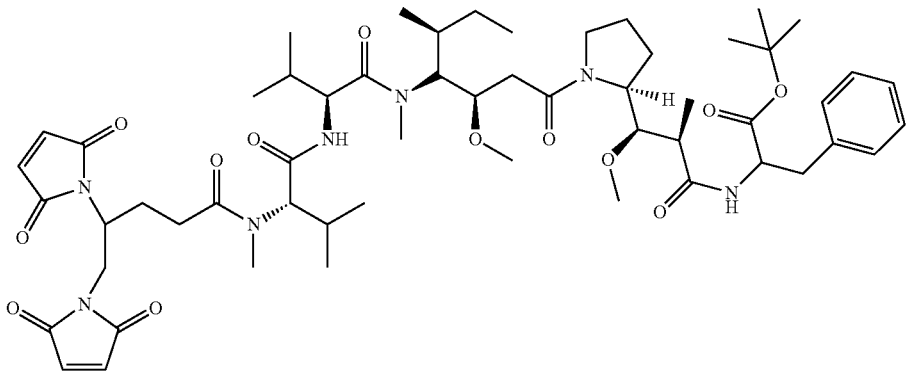

Compound 22 was prepared from compound 3, via the similar synthetic procedure as Example 7. LC-MS m/z (ES⁺), 1063.7 (M+H)⁺.

Example 17

Preparation of Compound 23

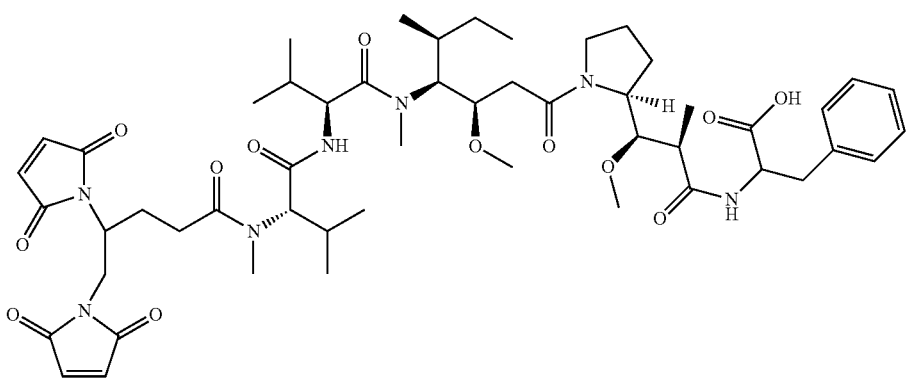 [SMILES: CC[C@H](C)[C@@H]([C@@H](CC(=O)N1CCC[C@H]1[C@H](OC)[C@@H](C)C(=O)NC(Cc1ccccc1)C(=O)O)OC)N(C)C(=O)[C@@H](NC(=O)[C@H](C(C)C)N(C)C(=O)CCC(CN1C(=O)C=CC1=O)N1C(=O)C=CC1=O)C(C)C]

Compound 23 was prepared from compound 22, via the similar synthetic procedure as Example 8. LC-MS m/z (ES⁺), 1006.4 (M+H)⁺.

Example 18

Preparation of Compound 24

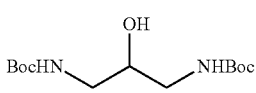

Compound 24 was prepared according to literature method (Chem. Eur. J. 2004, 10, 1215-1226).

Example 19

Preparation of Compound 25

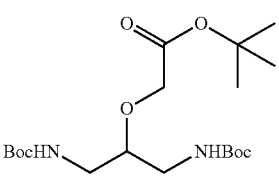 [SMILES: CC(C)(C)OC(=O)COC(CNC(=O)OC(C)(C)C)CNC(=O)OC(C)(C)C]

Bromo tert-butyl acetate (5.4 mL, 33.5 mmol) was added to a solution of compound 24 (3.9 g, 13.4 mmol) in dry THF (4 mL), Sodium hydride (60% wt in mineral oil, 2.42 g, 60.5 mmol) was added in portions in 1 h. The reaction mixture was stirred for 5 h and filtered through celite. Solvent was removed in vacuo, and the residue was purified by column chromatography (silica gel, petroleum ether/ethyl acetate 10/1 to 5/1) to give a white solid (3.9 g). LC-MS m/z (ES$^+$), 315.1 (M+H)$^+$.

Example 20

Preparation of Compound 26

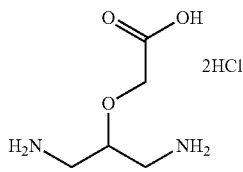

To a solution of compound 25 (1.0 g, 2.5 mmol) in 1,4-dioxane (10 mL) was added conc. HCl (5 mL). The reaction mixture was stirred at room temperature for 16 h. Solvent was removed in vacuo to afford a white solid (570 mg). The crude product was used for next step without further purification. LC-MS m/z (ES$^+$), 149.2 (M+H)$^+$.

Example 21

Preparation of Compound 4

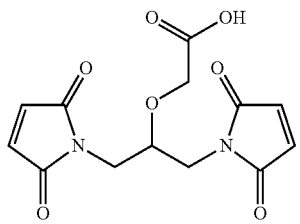 [SMILES: O=C(O)COC(CN1C(=O)C=CC1=O)CN1C(=O)C=CC1=O]

To a solution of compound 26 (250 mg, 1.1 mmol) in saturated sodium bicarbonate/THF (1:1 v/v, 20 mL) cooled at 0° C. was added N-methoxycarbonyl-maleimide (526 mg, 3.4 mmol). The reaction mixture was stirred at 0° C. for 10 min, warmed to room temperature and stirred for 3 h. The solution was acidified with conc. HCl to pH 2-3, and extracted with ethyl acetate (50 mL×2). The combined organic phase was washed with brine (20 mL), dried, and concentrated. The crude product was purified by preparative HPLC to afford the product (91 mg). LC-MS m/z (ES$^+$). 149.2 (M+H)$^+$; $^1$H NMR (DMSO-d$_6$) δ7.04; (s, 4H), 3.97; (s, 2H), 3.76-3.73; (m, 1H), 3.49-3.47; (m, 4H).

Example 22

Preparation of Compound 27

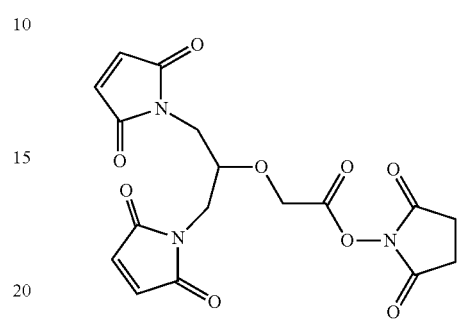

Compound 27 was prepared from compound 4, via the similar synthetic procedure as Example 3.

Example 23

Preparation of Compound 28

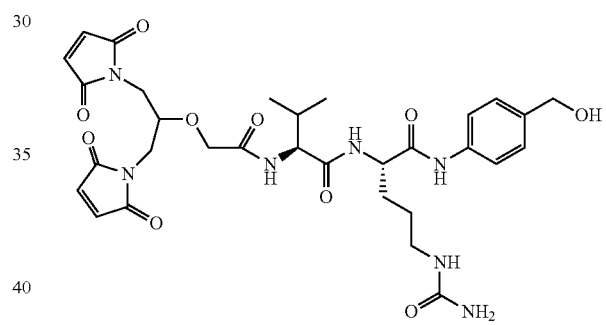

Compound 28 was prepared from compound 27, via the similar synthetic procedure as Example 4. LC-MS m/z (ES$^+$), 670.3 (M+H)$^+$.

Example 24

Preparation of Compound 29

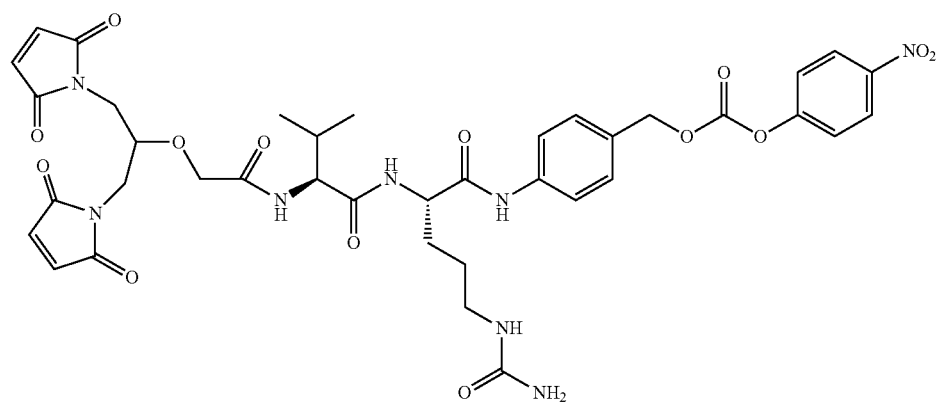 [SMILES: CC(C)[C@H](NC(=O)COC(CN1C(=O)C=CC1=O)CN1C(=O)C=CC1=O)C(=O)N[C@@H](CCCNC(N)=O)C(=O)Nc1ccc(COC(=O)Oc2ccc([N+](=O)[O-])cc2)cc1]

Compound 29 was prepared from compound 28, via the similar synthetic procedure as Example 5. LC-MS m/z (ES+), 835.2 (M+H)+.
Example 25
Preparation of Compound 30
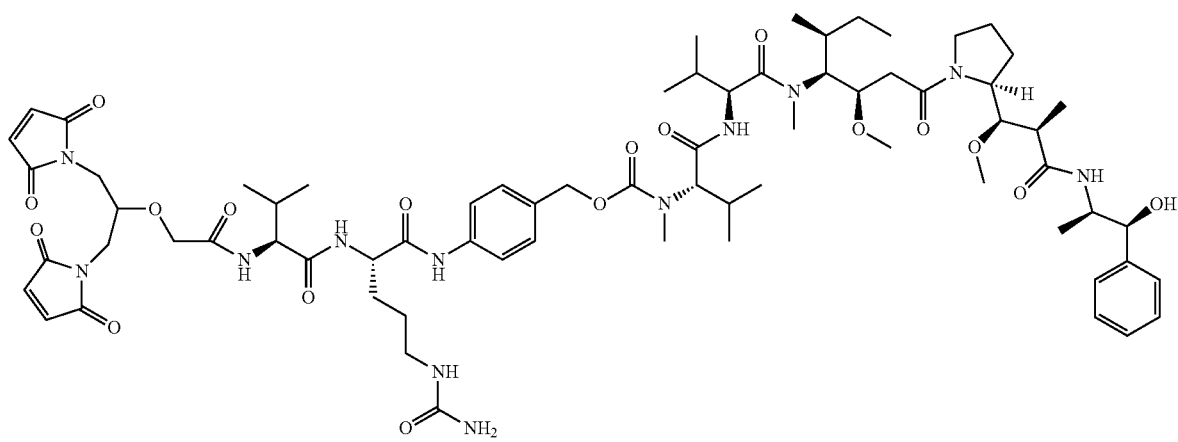 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(NC(=O)[C@H](CCCNC(N)=O)NC(=O)[C@@H](NC(=O)COC(CN2C(=O)C=CC2=O)CN2C(=O)C=CC2=O)C(C)C)cc1)C(C)C]
Compound 30 was prepared from compound 29, via the similar synthetic procedure as Example 6. LC-MS m/z (ES+), 707.5 ½(M+H)+.
Example 26
Preparation of Compound 31
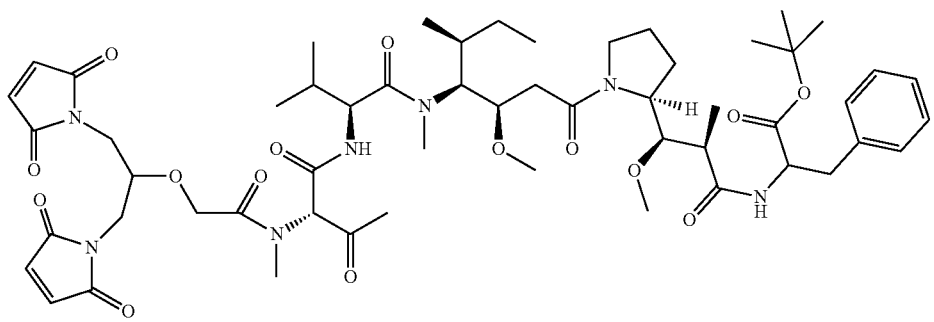 [SMILES: CC[C@H](C)[C@@H]([C@@H](CC(=O)N1CCC[C@H]1[C@H](OC)[C@@H](C)C(=O)NC(Cc1ccccc1)C(=O)OC(C)(C)C)OC)N(C)C(=O)[C@@H](NC(=O)[C@H](C(C)=O)N(C)C(=O)COC(CN1C(=O)C=CC1=O)CN1C(=O)C=CC1=O)C(C)C]

Compound 31 was prepared from compound 4, via the similar synthetic procedure as Example 7. LC-MS m/z (ES+). 1078.3 (M+H)+.

Example 27

Preparation of Compound 32

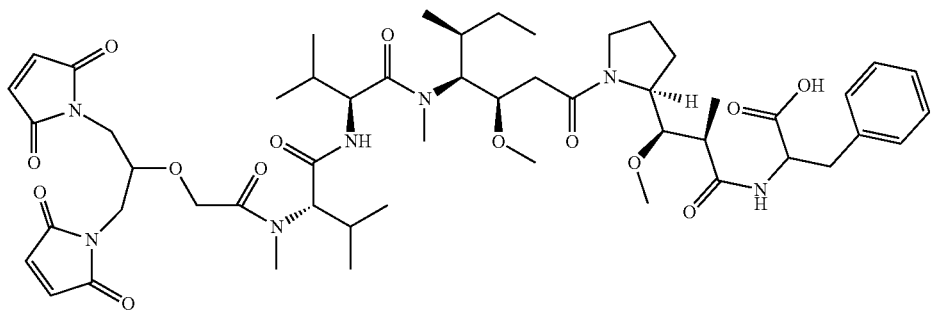 [SMILES: CC[C@H](C)[C@@H]([C@@H](CC(=O)N1CCC[C@H]1[C@H](OC)[C@@H](C)C(=O)NC(Cc1ccccc1)C(=O)O)OC)N(C)C(=O)[C@@H](NC(=O)[C@H](C(C)C)N(C)C(=O)COC(CN1C(=O)C=CC1=O)CN1C(=O)C=CC1=O)C(C)C]

Compound 32 was prepared from compound 31, via the similar synthetic procedure as Example 8, LC-MS m/z (ES+), 1022.3 (M+H)+.

Example 28

Preparation of Compound 33

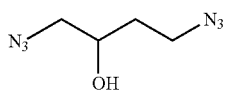

Compound 33 was prepared according to literature method (Bioorg. Med. Chem. Lett. 2003, 13, 3267-3271).

Example 29

Preparation of Compound 34

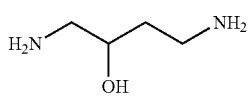

A solution of compound 33 (1.0 g, 6.4 mmol) and triphenylphosphine (4.0 g, 15.4 mmol) in THF (20 mL) and water (0.4 mL) was stirred at room temperature overnight. The mixture was filtered to remove the solid, and the filtrate was partitioned between diethyl ether and water. The aqueous phase was lyophilized to afford a colorless gel (580 mg).

Example 30

Preparation of Compound 35

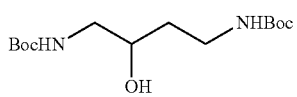

Compound 35 was prepared from compound 34, via the similar synthetic procedure as Example 18. LC-MS m/z (ES+) 327.2 (M+Na)+.

Example 31

Preparation of Compound 36

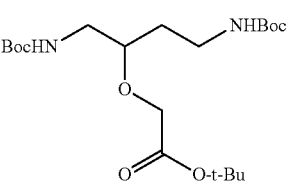

Compound 36 was prepared from compound 35, via the similar synthetic procedure as Example 19.

Example 32

Preparation of Compound 37

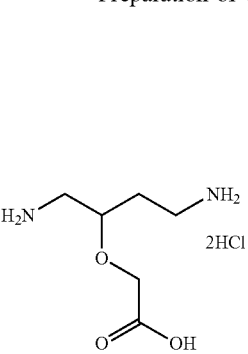

Compound 37 was prepared from compound 36, via the similar synthetic procedure as Example 20

Example 33

Preparation of Compound 5

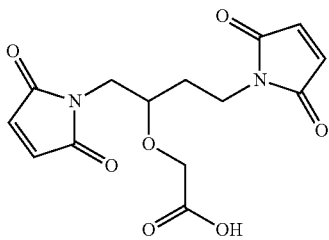 [SMILES: O=C(O)COC(CCN1C(=O)C=CC1=O)CN1C(=O)C=CC1=O]

Compound 5 was prepared from compound 37, via the similar synthetic procedure as Example 21. LC-MS m/z (ES+), 323.1 (M+H)+; ¹H NMR (CDCl₃) δ6.75; (s, 2H), 6.71; (s, 2H), 4.23; (s, 2H), 3.72-3.68; (m, 4H). 3.64-3.60; (m, 1H), 1.81-1.76; (m, 2H).

Example 34

Preparation of Compound 38

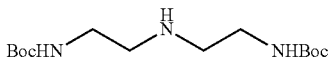

Compound 38 was prepared according to literature method (Org. Lett. 2000, 2, 14.)

Example 35

Preparation of Compound 39

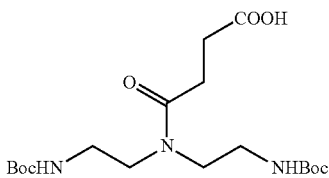 [SMILES: CC(C)(C)OC(=O)NCCN(CCNC(=O)OC(C)(C)C)C(=O)CCC(=O)O]

To a solution of compound 38 (2.0 g, 6.6 mmol) in DCM (30 mL) was added succinic anhydride (0.66 g, 6.6 mmol). The reaction mixture was stirred at room temperature for 16 h. Solvent was removed in vacuo, and the residue was purified by column chromatography (silica gel, DCM/MeOH 20/1) to afford a white solid (1.9 g). LC-MS m/z (ES+), 426.2 (M+Na)+.

Example 36

Preparation of Compound 40

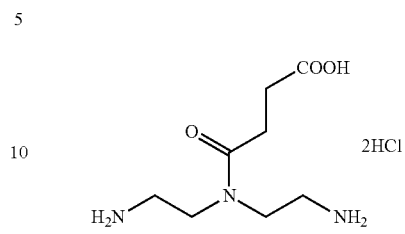

Compound 40 was prepared from compound 39, via the similar synthetic procedure as Example 20.

Example 37

Preparation of Compound 6

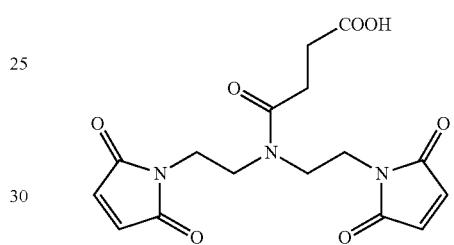

Compound 6 was prepared from compound 40, via the similar synthetic procedure as Example 21. ¹H NMR (DMSO-d₆) δ7.04; (s, 2H), 6.96; (s, 2H), 3.59; (t, 2H), 3.53; (t, 2H), 3.42-3.39; (m, 4H), 2.33; (s, 4H).

Example 38

Figure 2A:
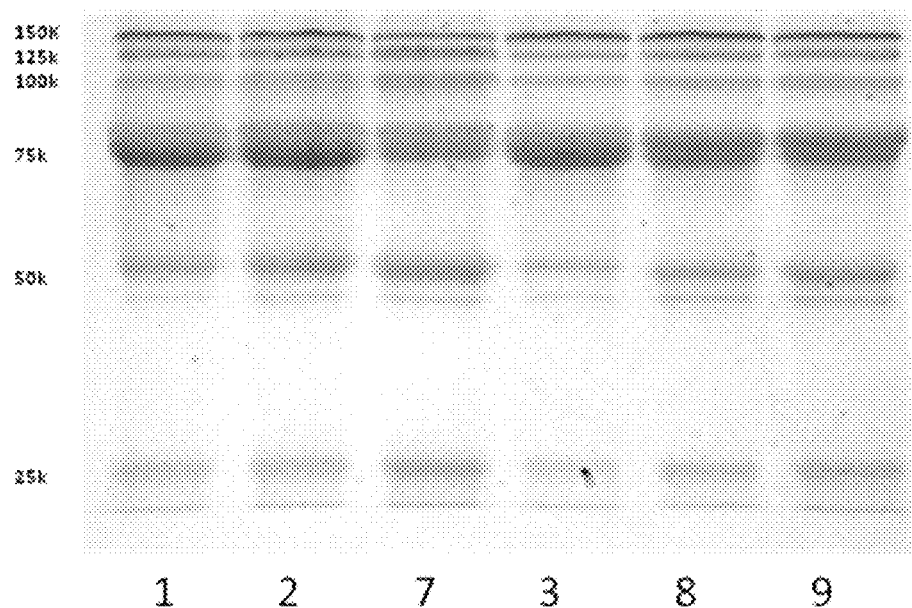
FIG. 2a shows the SDS-PAGE results for the antibody-tridentate (bidentate) linker conjugates 1, 2, 3, 7, 8 and 9.
Figure 2B:
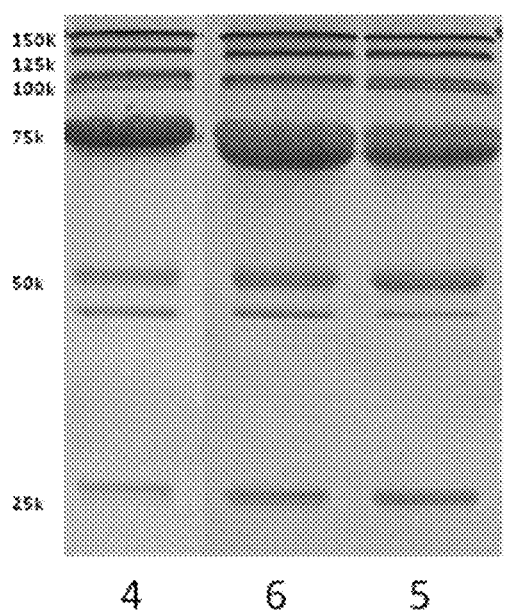
FIG. 2b shows the SDS-PAGE results for the antibody-tridentate (bidentate) linker conjugates 4, 5 and 6.
Figure 3A:
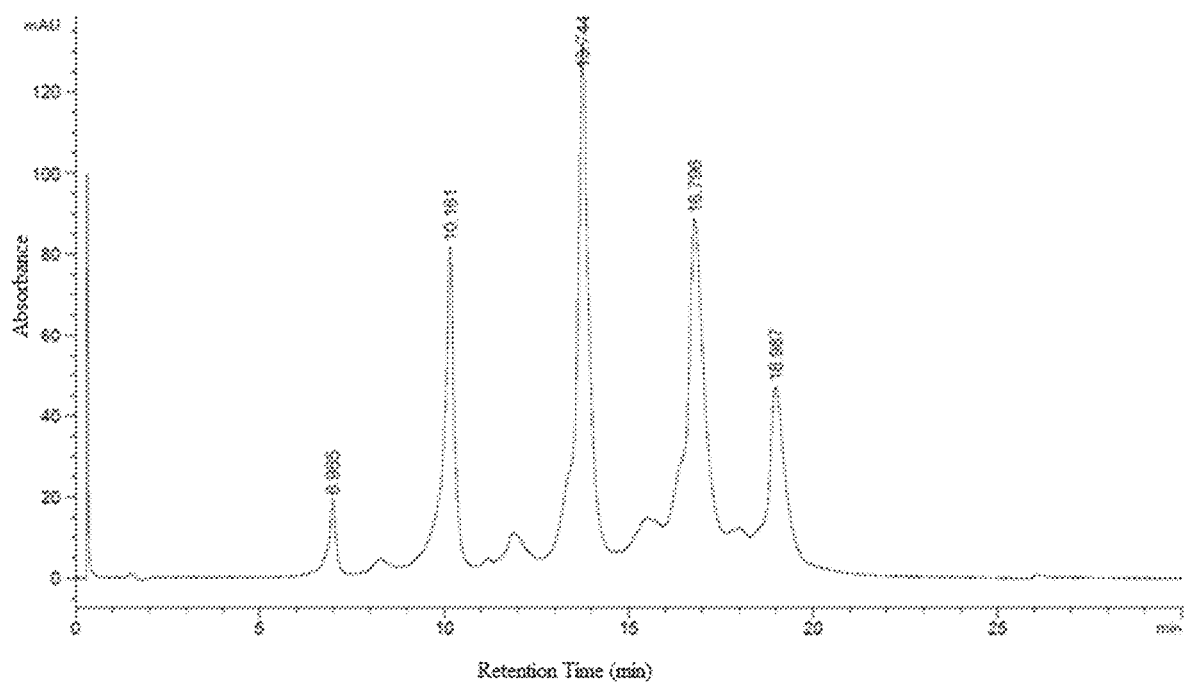
FIG. 3a shows the HIC results of antibody drug conjugate H-mc-vcMMAE.
Figure 3B:
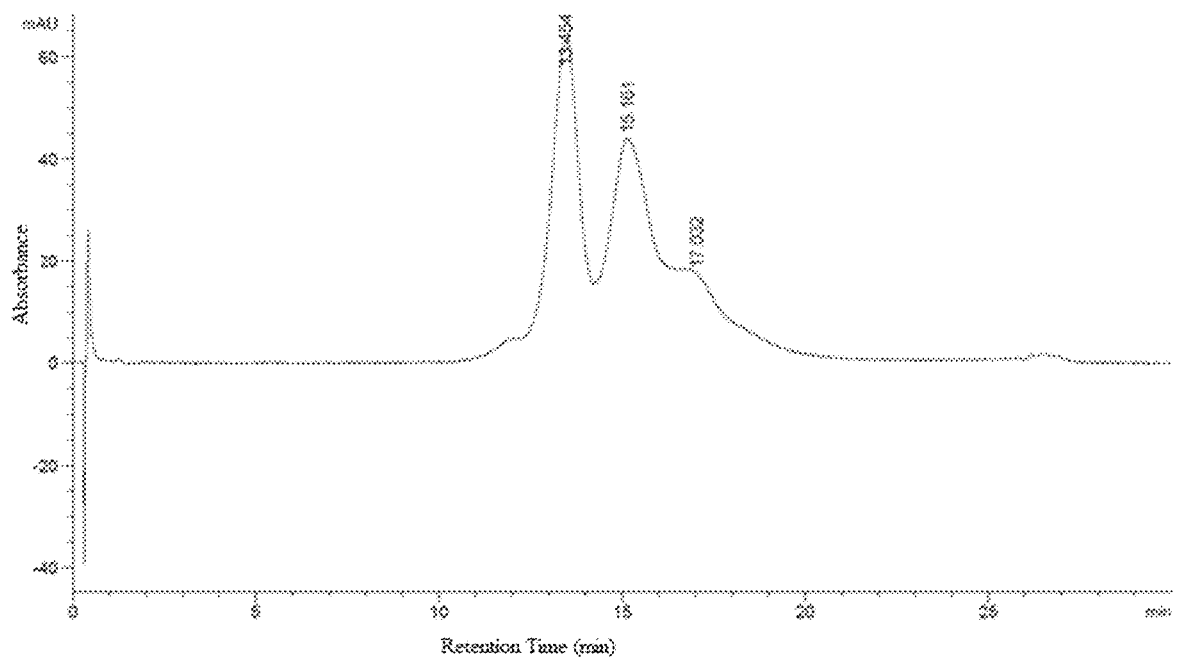
FIG. 3b shows the HIC results of antibody drag conjugate H-1-vcMMAE.
Figure 3C:
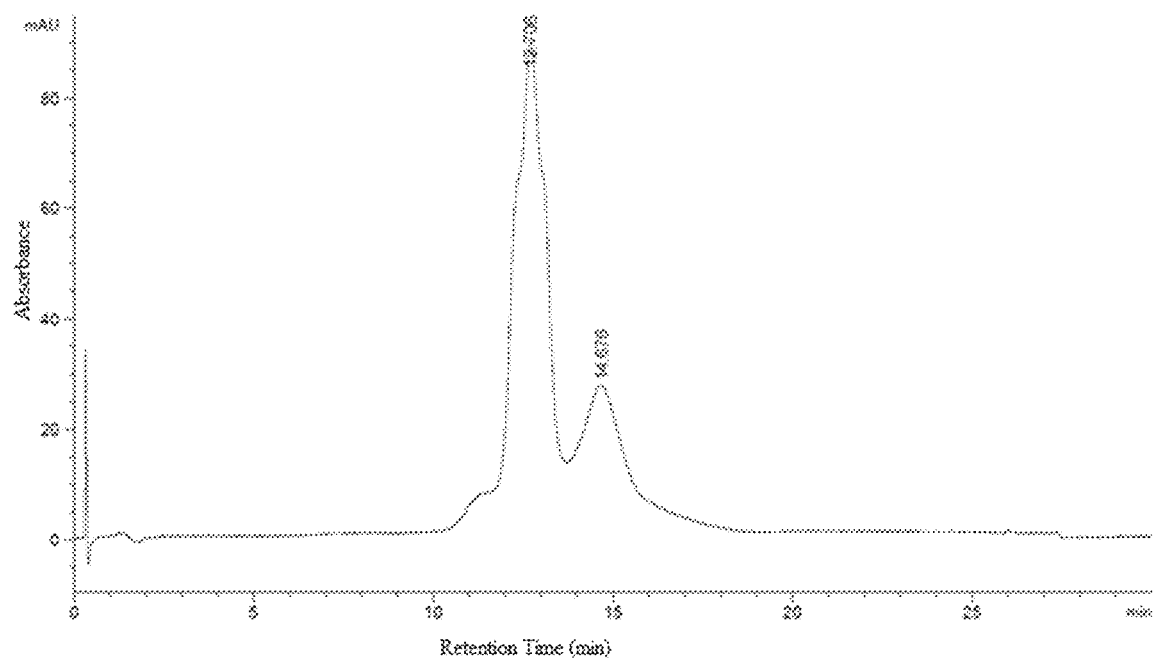
FIG. 3c shows the HIC results of antibody drug conjugate H-3-vcMMAE.
Figure 3D:
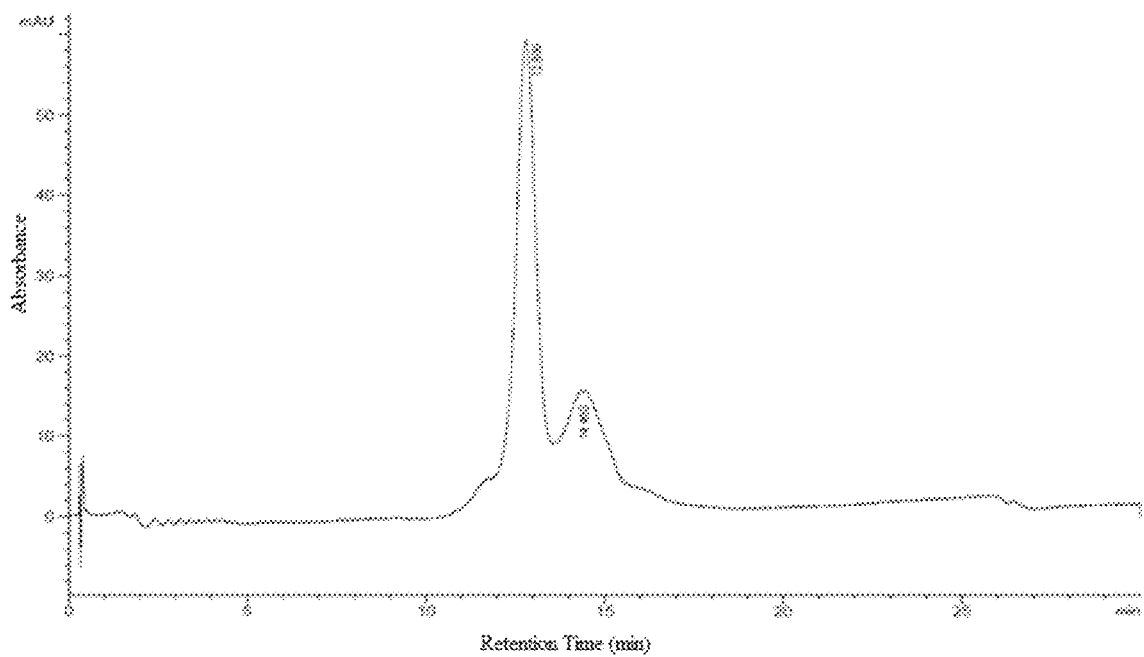
FIG. 3d shows the HIC results of antibody drag conjugate H-4-vcMMAE.
Figure 4A:
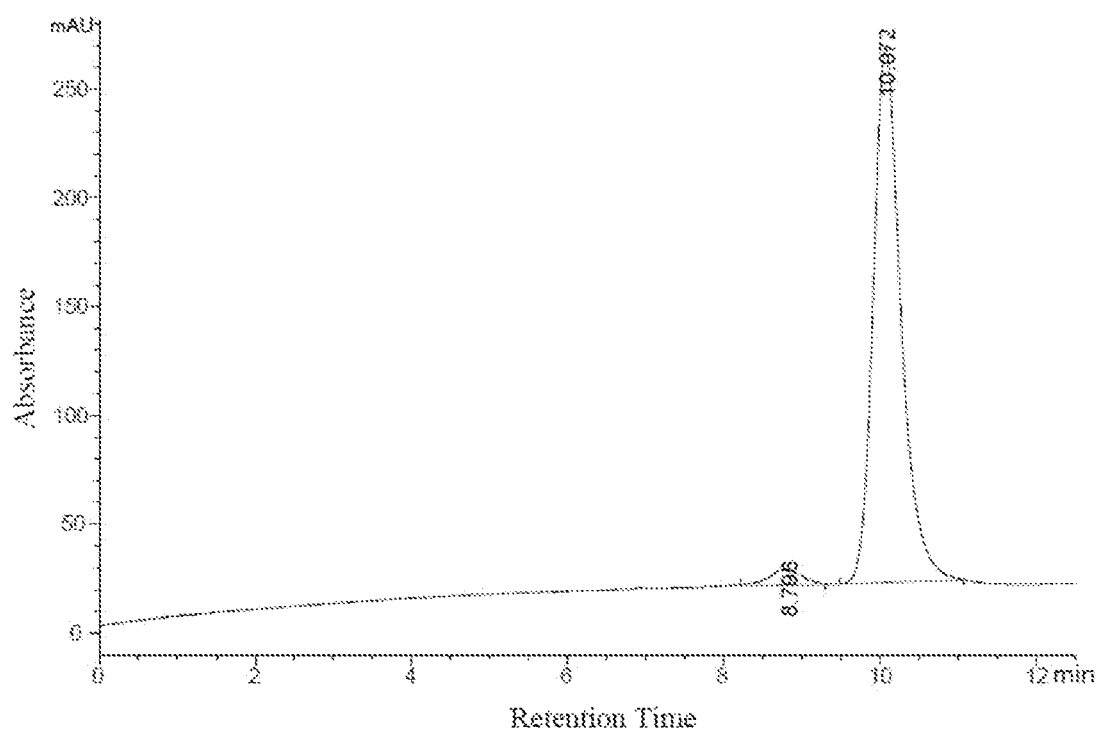
FIG. 4a shows the SEC results of antibody drug conjugate H-1-vcMMAE.
Figure 4B:
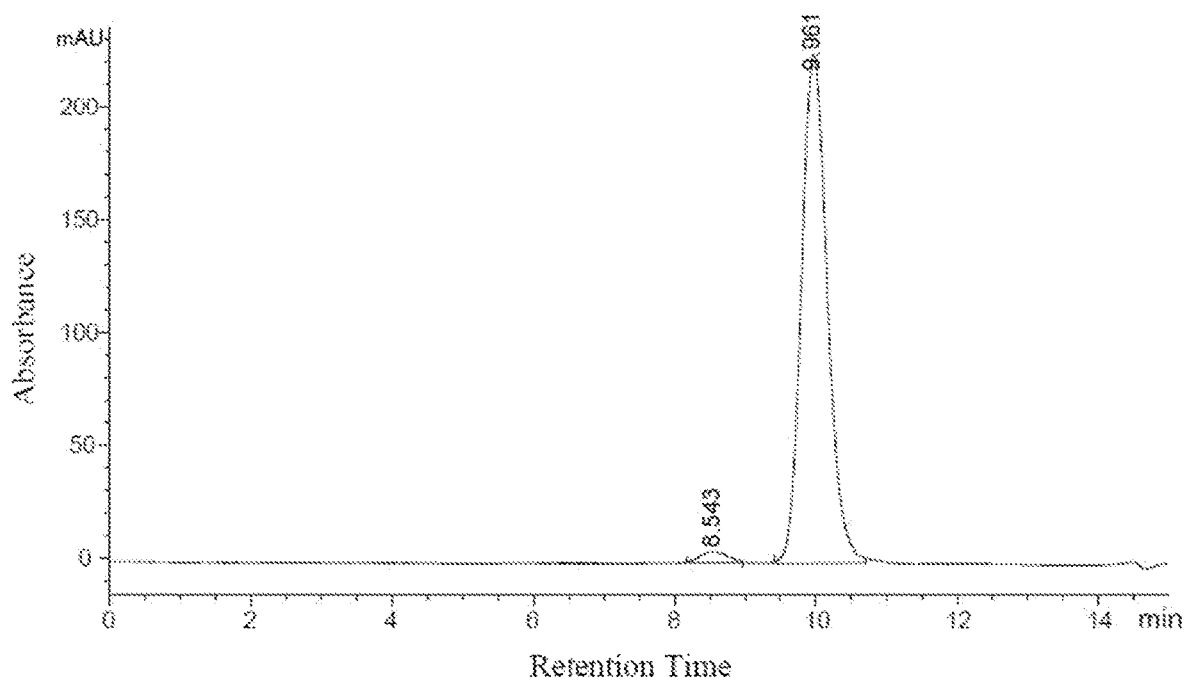
FIG. 4b shows the SEC results of antibody drug conjugate H-1-MMAF.
Figure 4C:
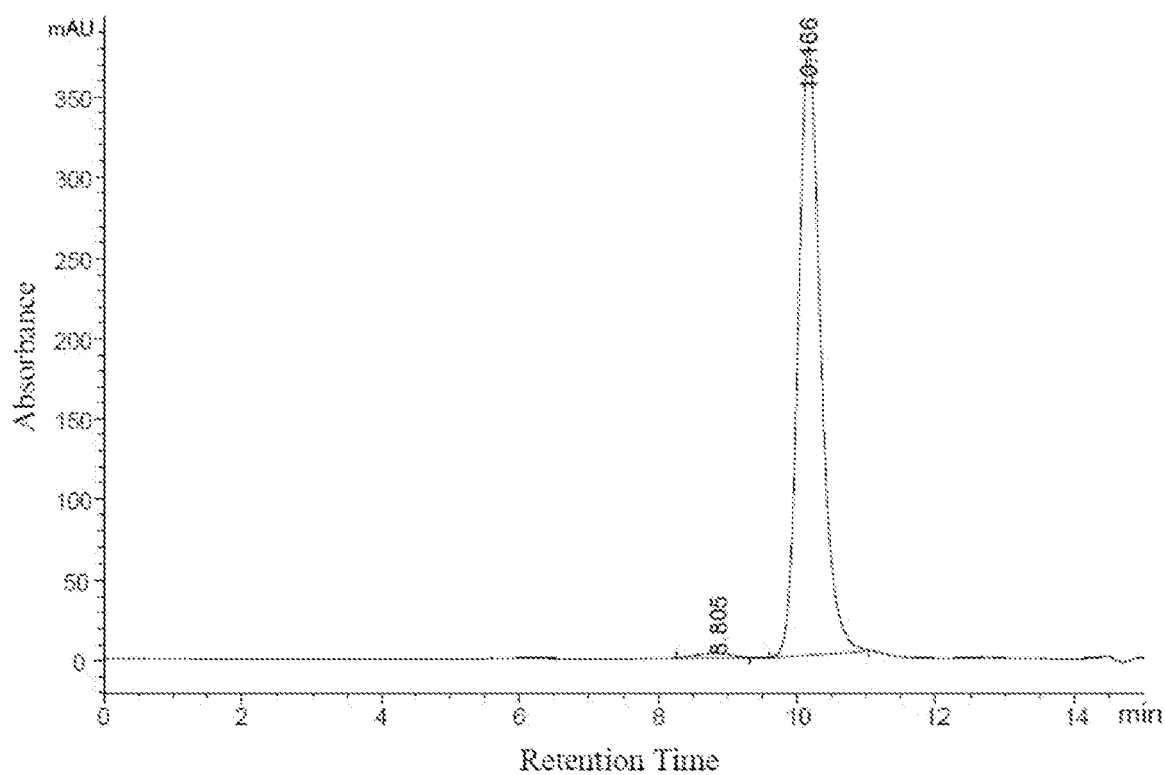
FIG. 4c shows the SEC results of antibody drug conjugate H-3-vcMMAE.
Figure 4D:
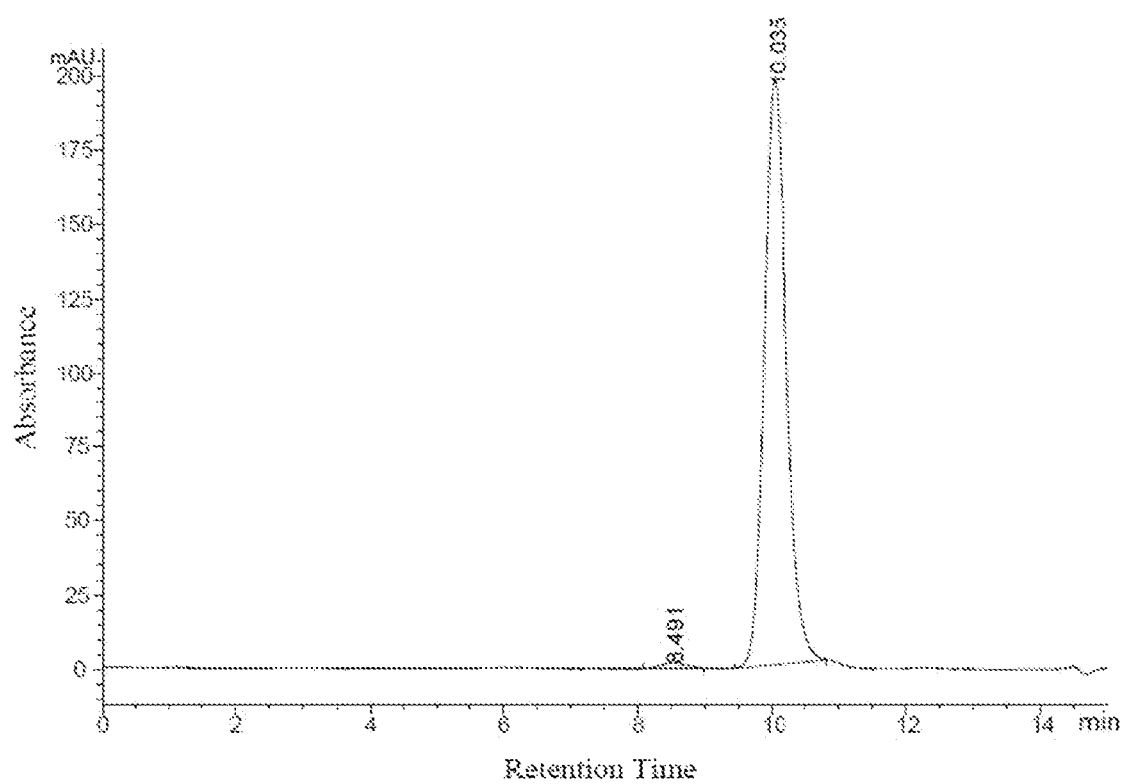
FIG. 4d shows the SEC results of antibody drug conjugate H-3-MMAF.
Figure 4E:
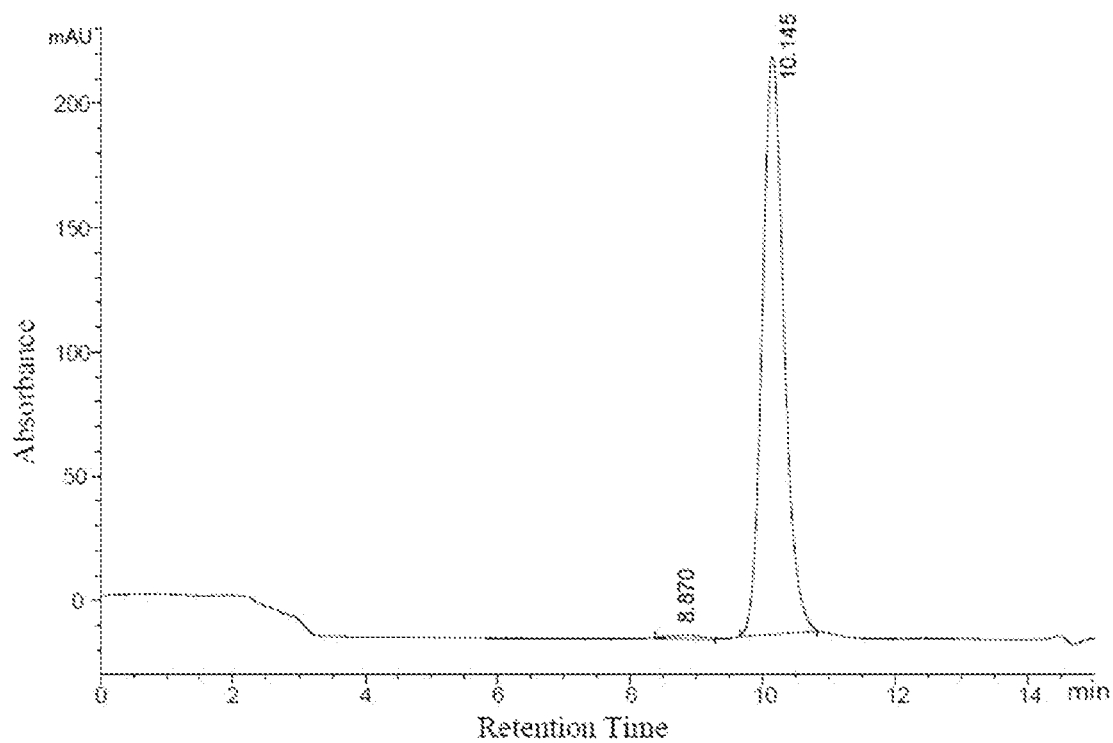
FIG. 4e shows the SEC results of antibody drug conjugate H-4-vcMMAE.
Figure 4F:
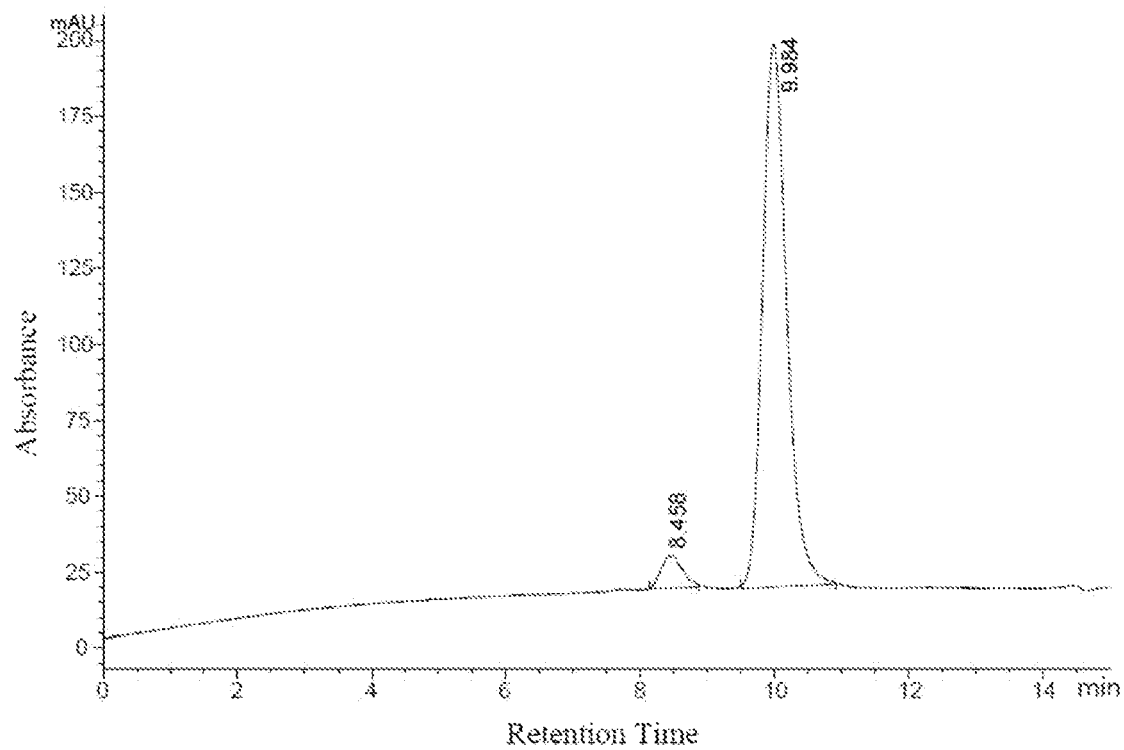
FIG. 4f shows the SEC results of antibody drug conjugate H-4-MMAF.
Figure 5A:
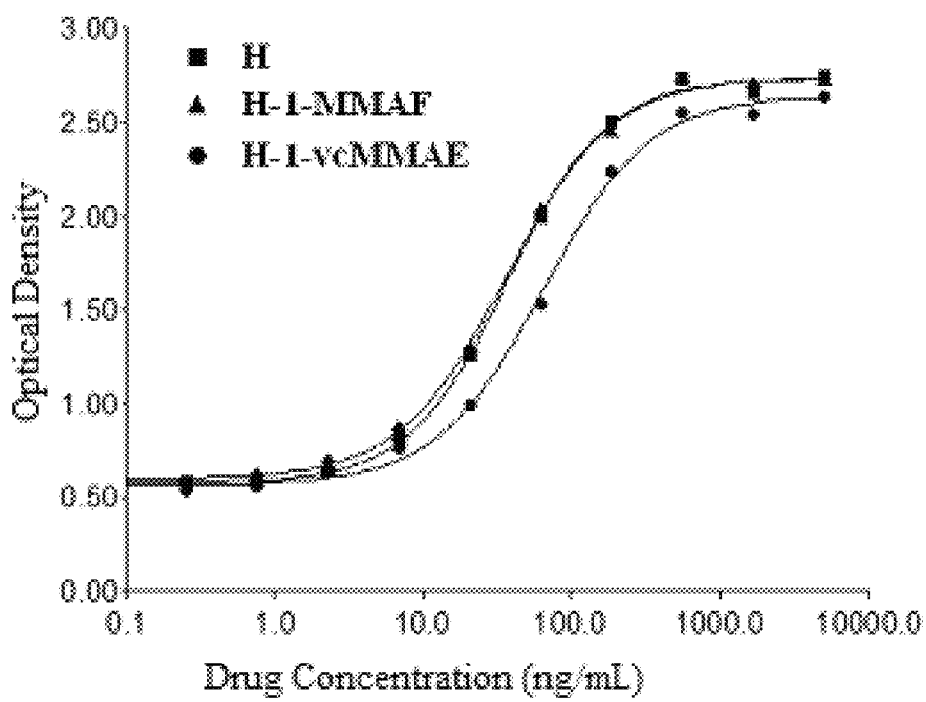
FIG. 5a shows the ELISA results of antibody drug conjugates H-1-MMAF and H-1-vcMMAE.
Figure 5B:
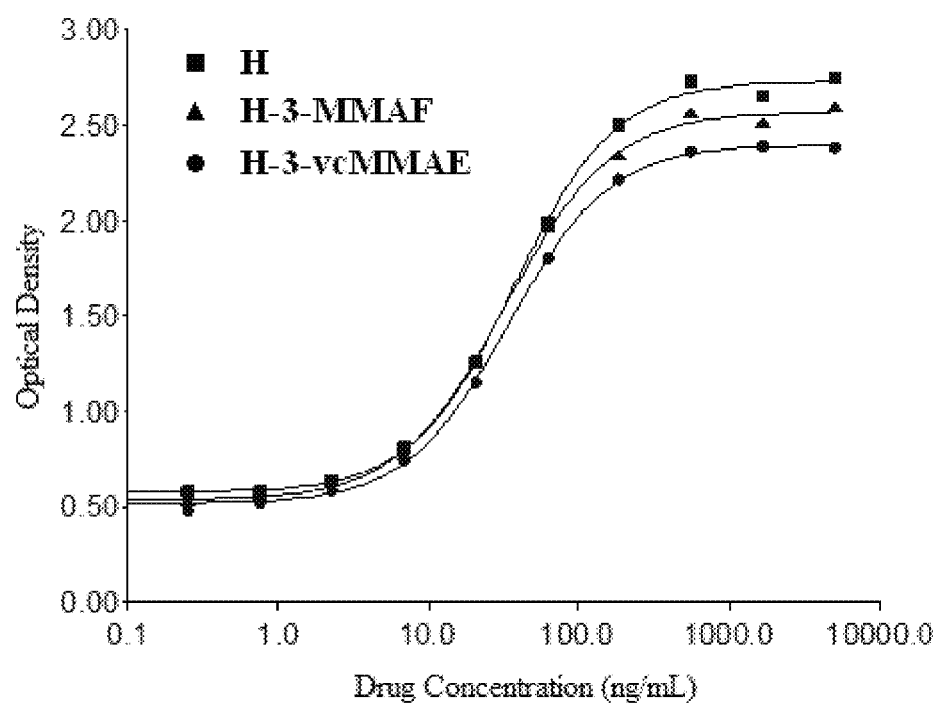
FIG. 5b shows the ELISA results of antibody drag conjugates H-3-MMAF and H-3-vcMMAE.
Figure 5C:
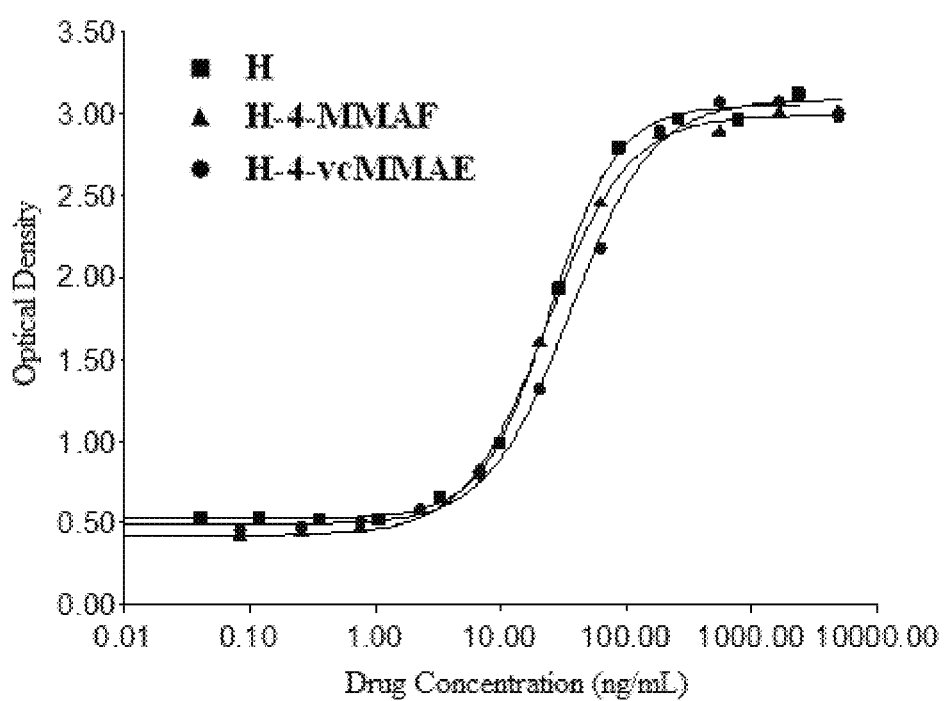
FIG. 5c shows the ELISA results of antibody drug conjugates H-4-MMAF and H-4-vcMMAE.
Figure 6A:
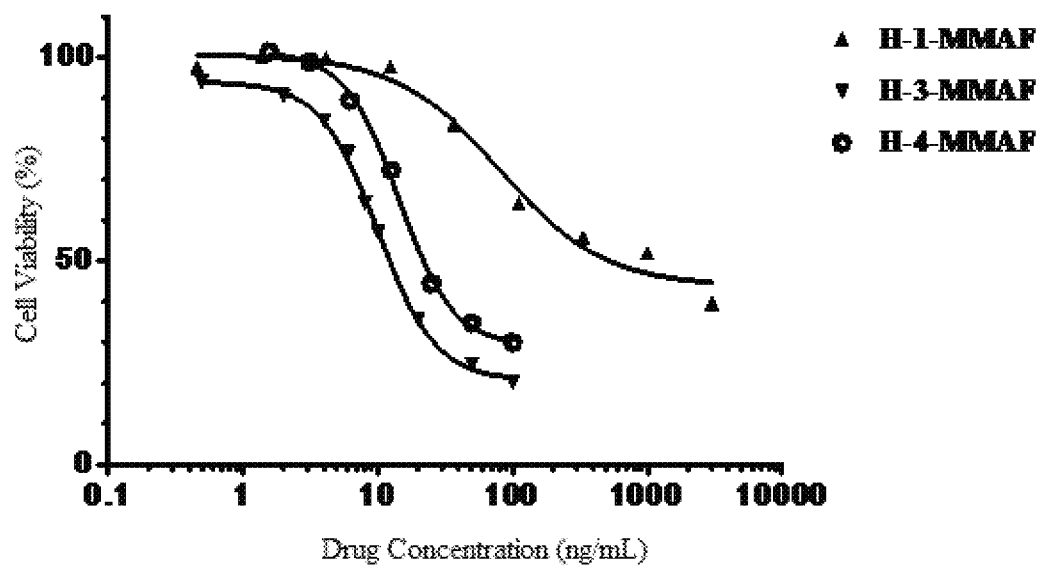
FIG. 6a shows the cell proliferation inhibition assay results of antibody drug conjugates, H-1-MMAF, H-3-MMAF and H-4-MMAF.
Figure 6B:
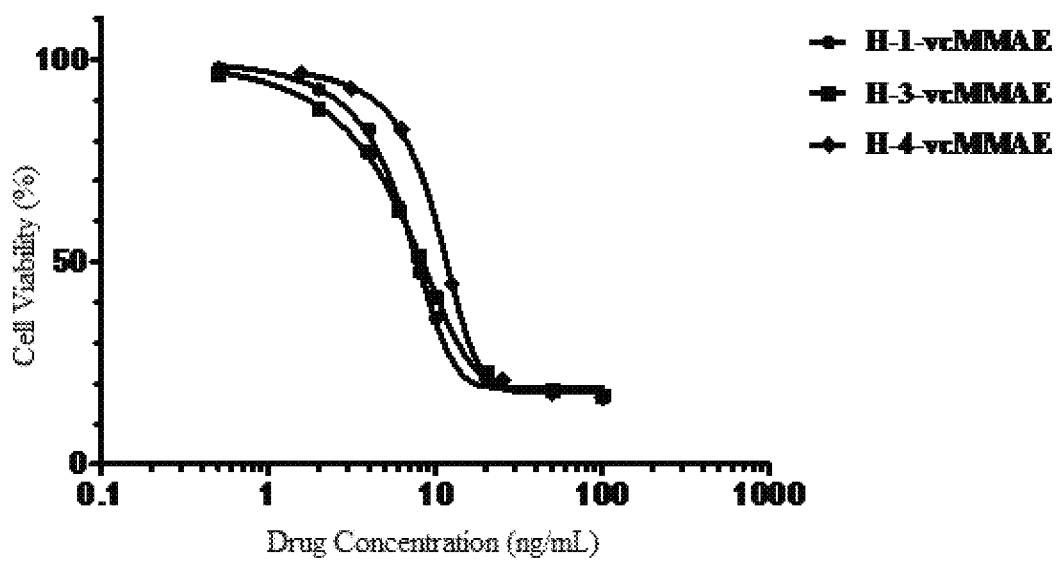
FIG. 6b shows the ceil proliferation inhibition assay results of antibody drug conjugates H-1-vcMMAE, H-3-vcMMAE, and H-4-vcMMAE.

The conjugation of antibody with linker 1, 7, 8, and 9 was carried out according to General Procedure B. FIG. 2 shows the effects of linker size and flexibility on the antibody-linker conjugation.

Example 39

Preparation of Antibody Drug Conjugate H-1-vcMMAE

The preparation of ADC H-1-vcMMAE was carried out according to General Procedure B.

Example 40

Preparation of Antibody Drug Conjugate H-1-MMAF

The preparation of H-1-MMAF was carried out according to General Procedure B.

Example 41

Preparation of Antibody Drug Conjugate H-3-vcMMAE

The preparation of ADC H-1-vcMMAE was carried out according to General Procedure B.

Example 42

Preparation of Antibody Drug Conjugate H-3-MMAF

The preparation of H-3-MMAF was carried out according to General Procedure B.

Example 43

Preparation of Antibody Drug Conjugate H-4-vcMMAE

The preparation of ADC H-4-vcMMAE was carried out according to General Procedure B.

Example 44

Preparation of Antibody Drug Conjugate H-4-MMAF

The preparation of H-4-MMAF was carried out according to General Procedure B.

Example 45

ELISA

The binding of antibody H (a herceptin biosimilar) and H-based antibody drug conjugates with antigen Her2 was measured by ELISA according to General Procedure E (Table 1), Compared to antibody H, H-based ADCs showed comparable antigen binding ability.

TABLE 1

| Sample | Binding Affinity ($EC_{50}$, ng/mL) |
|---|---|
| H | 32.5 |
| H-1-vcMMAE | 65.1 |
| H-1-MMAF | 37.7 |
| H-3-vcMMAE | 95.5 |
| H-3-MMAF | 32.3 |
| H-4-vcMMAE | 35.9 |
| H-4-MMAF | 23.3 |

Example 46

Cell Proliferation Assay

The potency of antibody H and H-based ADCs was measured by cell proliferation inhibition assay on human breast cancer cell line (SK-BR-3) according to General Procedure F (Table 2).

TABLE 2

| Sample | Cytotoxicity ($IC_{50}$, ng/mL) |
|---|---|
| H | 128 |
| H-1-vcMMAE | 6.7 |
| H-1-MMAF | 81.1 |
| H-3-vcMMAE | 7.1 |
| H-3-MMAF | 10.0 |
| H-4-vcMMAE | 10.1 |
| H-4-MMAF | 15.2 |

All literatures mentioned in the present invention were cited as references, exactly the same as each literature was cited independently as reference. It should be noted that the present invention could be modified by those in the art, which is also within the scope of the claims of the present invention.

What is claimed is:

1. The antibody drug conjugate wherein the antibody drug conjugate is as represented by formula VI, or VIII:

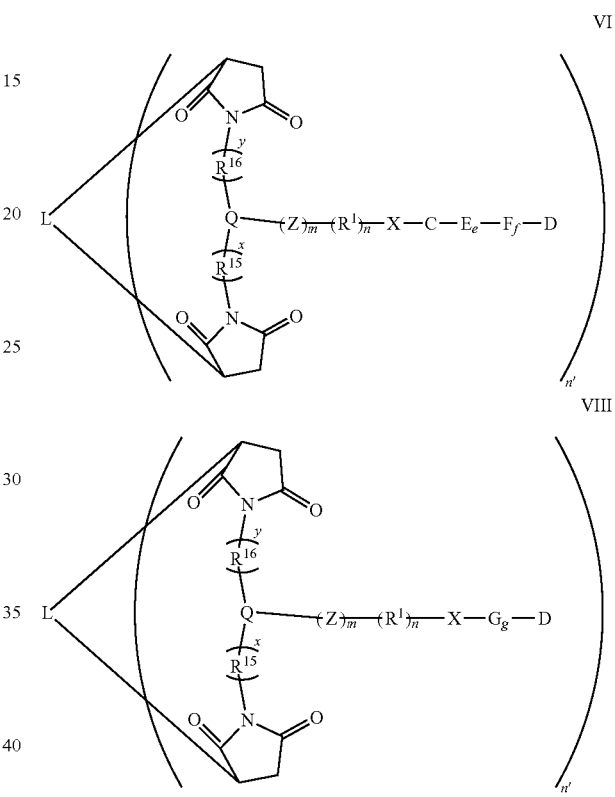

wherein
C is a cleavable linker;
E is a self-immolative linker;
F is an optional self-immolative linker;
G is a non-cleavable linker;
L is an antibody,
f is an integer of 0-5, g is an integer of 0-5, n' is an integer of 1-8; Z is O, S, $NR^2$, $C(=O)O$, $C(=O)NR^3$, $C(=S)O$, $C(=S)NR^4$, $C(=S)S$, $NR^5C(=O)NR^6$, $NR^7C(=S)NR^8$, $OC(=O)NR^9$; m is 0 or 1; $R^2$, $R^3$, $R^4$, $R^5$, $R^6$, $R^7$, $R^8$, and $R^9$ is independently selected from H, linear alkyl, cycloalkyl, heterocycloalkyl, alkenyl, alkynyl, aryl, heteroaryl; $R^1$ is linear alkyl, cycloalkyl, heterocycloalkyl, alkenyl, alkynyl, aryl, heteroaryl, poly(ethylene glycol) chain, or any combination thereof; n is an integer of 0-8; X is $-NR^{10}-$, $-O-$, $-S-$, $-C(=O)-$, $-C(=S)-$, $-NR^{11}C(=O)-$, $-NR^{12}C(=S)-$, $-OC(=O)-$, $-OC(=S)-$; $R^{10}$, $R^{11}$, and $R^{12}$ is independently selected from H, linear alkyl, cycloalkyl, heterocycloalkyl, alkenyl, alkynyl, aryl, heteroaryl; $R^{13}$ and $R^{14}$, is independently selected from linear alkyl, cycloalkyl, heterocycloalkyl, alkenyl, alkynyl, aryl, heteroaryl, or any combination thereof; $R^{15}$ and $R^{16}$ is independently selected from linear alkyl, cycloalkyl, heterocycloalkyl, alkenyl, aryl, heteroaryl, or any combination thereof; Q is N or $CR^{17}$; $R^{17}$ is independently selected from H, linear alkyl, cycloalkyl, heterocycloalkyl, alkenyl, alkynyl, x, y is an integer of 0-8, and x+y≥1; and D is a drug part.

2. The antibody drug conjugate of claim 1, wherein the antibody targets cell surface receptors or tumor-related antigens.

3. The antibody drug conjugate of claim 1, wherein the drug is cytotoxic drug, anti-autoimmune disease drug, or anti-inflammation drug.

4. The antibody drug conjugate of claim 1, wherein the average D:L ratio is about 4.

* * * * *